US009486328B2

(12) United States Patent　　(10) Patent No.: US 9,486,328 B2
Jimenez et al.　　(45) Date of Patent: Nov. 8, 2016

(54) EXPANDABLE INTERVERTEBRAL CAGE

(71) Applicant: Ex Technology, LLC, Gering, NE (US)

(72) Inventors: Omar F. Jimenez, Gering, NE (US); Yefim Safris, Golden Valley, MN (US)

(73) Assignee: Ex Technology, LLC, Gering, NE (US)

( * ) Notice: Subject to any disclaimer, the term of this patent is extended or adjusted under 35 U.S.C. 154(b) by 0 days.

(21) Appl. No.: 14/585,544

(22) Filed: Dec. 30, 2014

(65) Prior Publication Data

US 2015/0272743 A1　Oct. 1, 2015

Related U.S. Application Data

(63) Continuation-in-part of application No. 14/242,451, filed on Apr. 1, 2014, now Pat. No. 8,940,049.

(51) Int. Cl.
*A61F 2/44* (2006.01)
*A61B 17/88* (2006.01)
*A61F 2/30* (2006.01)

(52) U.S. Cl.
CPC ...... *A61F 2/447* (2013.01); *A61F 2002/30471* (2013.01); *A61F 2002/30507* (2013.01); *A61F 2002/30538* (2013.01); *A61F 2002/30556* (2013.01)

(58) Field of Classification Search
CPC .............. A61F 2/442–2/447; A61F 2/4611; A61F 2002/30471; A61F 2002/30411; A61F 2002/30538
USPC ............................................ 623/17.11–17.16
See application file for complete search history.

(56) References Cited

U.S. PATENT DOCUMENTS

| 283,218 A | 8/1883 | Rycke |
| 703,251 A | 6/1902 | Haire |
| 811,344 A | 1/1906 | Wands |
| 1,388,836 A | 8/1921 | Ripsch et al. |

(Continued)

FOREIGN PATENT DOCUMENTS

| EP | 1342456 A1 | 9/2003 |
| EP | 1552797 A2 | 7/2005 |

(Continued)

OTHER PUBLICATIONS

Website printout from https://seelio.com/w/fgf/omnilif-the-new-standard-in-spinal-deformity-correction-and-fusion?student=lumbarjax; dated Nov. 27, 2014, 5 pages.

(Continued)

*Primary Examiner* — Jacqueline Johanas
(74) *Attorney, Agent, or Firm* — Patterson Thuente Pedersen, P.A.

(57) ABSTRACT

An expandable intervertebral cage device includes a first base plate and a second base plate, a proximal block with internal threading that mechanically couples the first base plate and the second base plate, and a distal block comprising an internal passage. The device has exactly two arm assemblies, one on each side. Each arm assembly includes a first arm mechanically coupled to the first base plate and the distal block, and a second arm is mechanically coupled to the second base plate and the distal block. A screw is arranged partially within the internal threading of the proximal block and passes through the internal passage of the distal block, such that rotation of the screw relative to the proximal block causes a change in distance between the proximal block and the distal block, and a corresponding change in the spacing and lordosis of the device.

16 Claims, 18 Drawing Sheets

(56) References Cited

U.S. PATENT DOCUMENTS

| | | | |
|---|---|---|---|
| 1,500,859 A | 7/1924 | Wright | |
| 1,547,946 A | 7/1925 | Myers | |
| 2,106,088 A | 1/1938 | De Tar | |
| 2,231,221 A | 2/1941 | Rector | |
| 2,453,656 A | 11/1948 | Bullard, III | |
| 2,666,334 A | 1/1954 | Nalle | |
| 2,711,105 A | 6/1955 | Williams | |
| 2,842,976 A | 7/1958 | Young | |
| 2,891,408 A | 6/1959 | Burt, Jr. | |
| 3,386,128 A | 6/1968 | Vyvyan | |
| 3,449,971 A | 6/1969 | Posh | |
| 3,575,475 A | 4/1971 | Boerner | |
| 3,596,863 A | 8/1971 | Kaspareck | |
| 3,597,938 A | 8/1971 | Hellen | |
| 3,700,289 A | 10/1972 | Bilinski et al. | |
| 3,700,290 A | 10/1972 | Ensinger | |
| 3,708,925 A | 1/1973 | Ainoura | |
| 3,709,132 A | 1/1973 | Farrell et al. | |
| 3,916,596 A | 11/1975 | Hawley | |
| 3,985,000 A | 10/1976 | Hartz | |
| 3,988,906 A | 11/1976 | Smith | |
| 4,261,211 A | 4/1981 | Haberland | |
| 4,396,047 A | 8/1983 | Balkus | |
| 4,478,109 A | 10/1984 | Kobelt | |
| 4,516,303 A | 5/1985 | Kloster | |
| 4,528,864 A | 7/1985 | Craig | |
| 4,559,717 A | 12/1985 | Scire et al. | |
| 4,630,495 A | 12/1986 | Smith | |
| 4,691,586 A | 9/1987 | van Leijenhorst et al. | |
| 4,694,703 A | 9/1987 | Routson | |
| 4,869,552 A | 9/1989 | Tolleson et al. | |
| 5,133,108 A | 7/1992 | Esnault | |
| 5,172,442 A | 12/1992 | Bartley et al. | |
| 5,181,371 A | 1/1993 | Deworth | |
| 5,196,857 A | 3/1993 | Chiappetta et al. | |
| 5,198,932 A | 3/1993 | Takamura | |
| 5,222,986 A | 6/1993 | Wright | |
| 5,313,852 A | 5/1994 | Arena | |
| 5,374,556 A | 12/1994 | Bennett et al. | |
| 5,439,377 A | 8/1995 | Milanovich | |
| 5,445,471 A | 8/1995 | Wexler et al. | |
| 5,554,191 A * | 9/1996 | Lahille | A61B 17/1757 411/55 |
| 5,645,599 A | 7/1997 | Samani | |
| 5,653,763 A * | 8/1997 | Errico | A61F 2/446 411/55 |
| 5,664,457 A | 9/1997 | Nejati | |
| 5,904,479 A | 5/1999 | Staples | |
| 5,960,670 A | 10/1999 | Iverson et al. | |
| 5,980,252 A | 11/1999 | Samchukov et al. | |
| 5,988,006 A | 11/1999 | Fleytman | |
| 6,039,761 A * | 3/2000 | Li et al. | A61B 17/70 623/17.16 |
| 6,045,579 A | 4/2000 | Hochshuler et al. | |
| 6,056,491 A | 5/2000 | Hsu | |
| 6,080,193 A * | 6/2000 | Hochshuler | A61F 2/4455 623/17.16 |
| 6,136,031 A | 10/2000 | Middleton | |
| 6,175,989 B1 | 1/2001 | Carpentar et al. | |
| 6,315,797 B1 | 11/2001 | Middleton | |
| 6,350,317 B1 | 2/2002 | Hao et al. | |
| 6,378,172 B1 | 4/2002 | Schrage | |
| 6,395,035 B2 | 5/2002 | Bresina et al. | |
| 6,454,806 B1 | 9/2002 | Cohen et al. | |
| 6,454,807 B1 * | 9/2002 | Jackson | A61F 2/447 623/17.15 |
| 6,484,608 B1 | 11/2002 | Ziavras | |
| 6,517,772 B1 | 2/2003 | Woolf | |
| 6,554,526 B1 | 4/2003 | Egelandsdal | |
| 6,616,695 B1 | 9/2003 | Crozet et al. | |
| 6,641,614 B1 | 11/2003 | Wagner et al. | |
| 6,719,796 B2 | 4/2004 | Cohen et al. | |
| 6,752,832 B2 | 6/2004 | Neumann | |
| 6,772,479 B2 | 8/2004 | Hinkley et al. | |
| 6,802,229 B1 | 10/2004 | Lambert | |
| 6,808,537 B2 | 10/2004 | Michelson | |
| 6,863,673 B2 | 3/2005 | Gerbec et al. | |
| 6,932,844 B2 | 8/2005 | Ralph et al. | |
| 6,953,477 B2 | 10/2005 | Berry | |
| 7,018,415 B1 | 3/2006 | McKay | |
| 7,051,610 B2 | 5/2006 | Stoianovici et al. | |
| 7,070,598 B2 | 7/2006 | Lim et al. | |
| 7,087,055 B2 | 8/2006 | Lim et al. | |
| 7,201,751 B2 | 4/2007 | Zucherman et al. | |
| 7,273,373 B2 | 9/2007 | Horiuchi | |
| 7,308,747 B2 | 12/2007 | Smith et al. | |
| 7,316,381 B2 | 1/2008 | Häcker et al. | |
| 7,410,201 B1 | 8/2008 | Wilson et al. | |
| 7,425,103 B2 | 9/2008 | Perez-Sanchez | |
| 7,431,735 B2 * | 10/2008 | Liu | A61F 2/446 623/17.11 |
| 7,435,032 B1 | 10/2008 | Murphey et al. | |
| 7,547,325 B2 | 6/2009 | Biedermann et al. | |
| 7,584,682 B2 | 9/2009 | Hsiao | |
| 7,611,538 B2 | 11/2009 | Belliard et al. | |
| 7,632,281 B2 | 12/2009 | Errico et al. | |
| 7,674,296 B2 | 3/2010 | Rhoda et al. | |
| 7,682,376 B2 | 3/2010 | Trieu | |
| 7,708,779 B2 | 5/2010 | Edie et al. | |
| 7,712,389 B2 | 5/2010 | Wang | |
| 7,753,958 B2 | 7/2010 | Gordon et al. | |
| 7,758,645 B2 | 7/2010 | Studer | |
| 7,758,648 B2 | 7/2010 | Castleman et al. | |
| 7,892,285 B2 | 2/2011 | Viker | |
| 7,896,919 B2 | 3/2011 | Belliard et al. | |
| 7,901,409 B2 * | 3/2011 | Canaveral | A61B 17/8858 600/222 |
| 7,947,078 B2 | 5/2011 | Siegal | |
| 7,985,256 B2 | 7/2011 | Grotz et al. | |
| 8,057,549 B2 | 11/2011 | Butterman et al. | |
| 8,070,813 B2 | 12/2011 | Grotz et al. | |
| 8,088,163 B1 | 1/2012 | Kleiner | |
| 8,192,495 B2 | 6/2012 | Simpson et al. | |
| 8,303,663 B2 | 11/2012 | Jimenez et al. | |
| 8,496,706 B2 * | 7/2013 | Ragab | A61F 2/4425 623/17.11 |
| 8,523,944 B2 | 9/2013 | Jimenez et al. | |
| 8,540,452 B2 | 9/2013 | Jimenez et al. | |
| 8,628,577 B1 | 1/2014 | Jimenez | |
| 8,636,746 B2 | 1/2014 | Jimenez et al. | |
| 8,771,360 B2 | 7/2014 | Jimenez et al. | |
| 8,795,366 B2 * | 8/2014 | Varela | A61F 2/447 623/17.11 |
| 8,894,712 B2 * | 11/2014 | Varela | A61F 2/447 623/17.16 |
| 8,906,100 B2 | 12/2014 | Jimenez | |
| 8,932,302 B2 | 1/2015 | Jimenez et al. | |
| 8,940,049 B1 * | 1/2015 | Jimenez | A61F 2/447 623/17.15 |
| 2002/0128716 A1 * | 9/2002 | Cohen | A61F 2/44 623/17.15 |
| 2002/0138146 A1 | 9/2002 | Jackson | |
| 2003/0077110 A1 | 4/2003 | Knowles | |
| 2003/0233145 A1 | 12/2003 | Landry et al. | |
| 2004/0049271 A1 | 3/2004 | Biedermann et al. | |
| 2004/0111157 A1 | 6/2004 | Ralph et al. | |
| 2004/0153156 A1 | 8/2004 | Cohen et al. | |
| 2004/0225364 A1 | 11/2004 | Richelsoph et al. | |
| 2005/0000228 A1 | 1/2005 | De Sousa et al. | |
| 2005/0033431 A1 | 2/2005 | Gordon et al. | |
| 2005/0095384 A1 | 5/2005 | Wittmeyer, Jr. | |
| 2005/0113921 A1 | 5/2005 | An et al. | |
| 2005/0113924 A1 | 5/2005 | Buttermann | |
| 2005/0175406 A1 | 8/2005 | Perez-Sanchez | |
| 2005/0182416 A1 | 8/2005 | Lim et al. | |
| 2005/0261769 A1 | 11/2005 | Moskowitz et al. | |
| 2006/0004447 A1 | 1/2006 | Mastrorio et al. | |
| 2006/0004455 A1 | 1/2006 | Leonard et al. | |
| 2006/0025862 A1 | 2/2006 | Villiers et al. | |
| 2006/0058878 A1 * | 3/2006 | Michelson | A61F 2/446 623/17.11 |
| 2006/0129244 A1 | 6/2006 | Ensign | |
| 2006/0149385 A1 | 7/2006 | McKay | |
| 2006/0184171 A1 | 8/2006 | Biedermann et al. | |

(56) References Cited

U.S. PATENT DOCUMENTS

| | | | |
|---|---|---|---|
| 2006/0247781 A1 | 11/2006 | Francis | |
| 2006/0253201 A1* | 11/2006 | McLuen | A61F 2/4455 623/17.15 |
| 2006/0293752 A1 | 12/2006 | Mounmene et al. | |
| 2007/0032791 A1 | 2/2007 | Greenhalgh et al. | |
| 2007/0049943 A1 | 3/2007 | Moskowitz et al. | |
| 2007/0083267 A1 | 4/2007 | Miz et al. | |
| 2007/0093901 A1 | 4/2007 | Grotz et al. | |
| 2007/0129730 A1 | 6/2007 | Woods et al. | |
| 2007/0185577 A1 | 8/2007 | Malek | |
| 2007/0191954 A1 | 8/2007 | Hansell et al. | |
| 2007/0191958 A1 | 8/2007 | Abdou | |
| 2007/0198089 A1 | 8/2007 | Moskowitz et al. | |
| 2007/0219634 A1 | 9/2007 | Greenhalgh et al. | |
| 2007/0222100 A1 | 9/2007 | Husted et al. | |
| 2007/0250171 A1 | 10/2007 | Bonin, Jr. | |
| 2007/0255415 A1 | 11/2007 | Edie et al. | |
| 2007/0282449 A1 | 12/2007 | de Villiers et al. | |
| 2007/0288092 A1 | 12/2007 | Bambakidis | |
| 2007/0293329 A1 | 12/2007 | Glimpel et al. | |
| 2007/0293948 A1 | 12/2007 | Bagga et al. | |
| 2008/0026903 A1 | 1/2008 | Flugrad et al. | |
| 2008/0077246 A1 | 3/2008 | Fehling et al. | |
| 2008/0091211 A1 | 4/2008 | Gately | |
| 2008/0100179 A1 | 5/2008 | Ruggeri et al. | |
| 2008/0103601 A1 | 5/2008 | Biro et al. | |
| 2008/0114367 A1* | 5/2008 | Meyer | A61B 17/025 606/90 |
| 2008/0140207 A1 | 6/2008 | Olmos et al. | |
| 2008/0147194 A1 | 6/2008 | Grotz et al. | |
| 2008/0154266 A1 | 6/2008 | Protopsaltis et al. | |
| 2008/0161920 A1 | 7/2008 | Melkent | |
| 2008/0161931 A1 | 7/2008 | Perez-Cruet et al. | |
| 2008/0168855 A1 | 7/2008 | Giefer et al. | |
| 2008/0183204 A1 | 7/2008 | Greenhalgh et al. | |
| 2008/0188941 A1 | 8/2008 | Grotz | |
| 2008/0210039 A1 | 9/2008 | Brun | |
| 2008/0221694 A1 | 9/2008 | Warnick et al. | |
| 2008/0234736 A1 | 9/2008 | Trieu et al. | |
| 2008/0281423 A1 | 11/2008 | Sheffer et al. | |
| 2008/0292392 A1 | 11/2008 | Voellmer | |
| 2008/0319487 A1 | 12/2008 | Fielding et al. | |
| 2009/0012564 A1 | 1/2009 | Chirico et al. | |
| 2009/0076614 A1 | 3/2009 | Arramon | |
| 2009/0099568 A1* | 4/2009 | Lowry | A61B 17/025 606/90 |
| 2009/0164017 A1 | 6/2009 | Sommerich et al. | |
| 2009/0210061 A1 | 8/2009 | Sledge | |
| 2009/0222100 A1 | 9/2009 | Cipoletti et al. | |
| 2009/0234362 A1 | 9/2009 | Blain et al. | |
| 2009/0259316 A1* | 10/2009 | Ginn | A61B 17/7062 623/17.16 |
| 2009/0299478 A1* | 12/2009 | Carls | A61F 2/4425 623/17.16 |
| 2009/0306672 A1 | 12/2009 | Reindel et al. | |
| 2010/0004688 A1 | 1/2010 | Maas et al. | |
| 2010/0076557 A1 | 3/2010 | Miller | |
| 2010/0082109 A1 | 4/2010 | Greenhalgh et al. | |
| 2010/0094305 A1 | 4/2010 | Chang et al. | |
| 2010/0161062 A1* | 6/2010 | Foley | A61F 2/4455 623/17.16 |
| 2010/0185291 A1* | 7/2010 | Jimenez | F16C 11/12 623/17.16 |
| 2010/0192715 A1 | 8/2010 | Vauchel et al. | |
| 2010/0209184 A1 | 8/2010 | Jimenez et al. | |
| 2011/0015638 A1* | 1/2011 | Pischl | A61B 17/025 606/90 |
| 2011/0054616 A1 | 3/2011 | Kamran et al. | |
| 2011/0093075 A1 | 4/2011 | Duplessis et al. | |
| 2011/0112644 A1 | 5/2011 | Zilberstein et al. | |
| 2011/0138948 A1 | 6/2011 | Jimenez et al. | |
| 2011/0160861 A1 | 6/2011 | Jimenez et al. | |
| 2011/0172774 A1* | 7/2011 | Varela | A61F 2/447 623/17.16 |
| 2011/0270398 A1 | 11/2011 | Grotz et al. | |
| 2012/0010653 A1* | 1/2012 | Seifert | A61B 17/0057 606/213 |
| 2012/0029636 A1* | 2/2012 | Ragab | A61F 2/4425 623/17.11 |
| 2012/0116518 A1 | 5/2012 | Grotz et al. | |
| 2012/0158071 A1 | 6/2012 | Jimenez et al. | |
| 2012/0185049 A1* | 7/2012 | Varela | A61F 2/447 623/17.16 |
| 2012/0226357 A1* | 9/2012 | Varela | A61F 2/447 623/17.16 |
| 2012/0271419 A1* | 10/2012 | Marik | A61F 2/4425 623/17.12 |
| 2012/0290094 A1 | 11/2012 | Lim et al. | |
| 2012/0303124 A1* | 11/2012 | McLuen | A61F 2/4455 623/17.16 |
| 2012/0323329 A1 | 12/2012 | Jimenez et al. | |
| 2013/0053966 A1 | 2/2013 | Jimenez et al. | |
| 2013/0144388 A1* | 6/2013 | Emery | A61B 17/025 623/17.16 |
| 2013/0158664 A1* | 6/2013 | Palmatier | A61F 2/447 623/17.16 |
| 2013/0197642 A1* | 8/2013 | Ernst | A61F 2/4465 623/17.16 |
| 2013/0317615 A1 | 11/2013 | Jimenez et al. | |
| 2014/0012383 A1 | 1/2014 | Triplett et al. | |
| 2014/0018924 A1* | 1/2014 | McManus | A61F 2/44 623/17.16 |
| 2014/0039622 A1 | 2/2014 | Glerum et al. | |
| 2014/0088714 A1* | 3/2014 | Miller | A61F 2/4425 623/17.16 |
| 2014/0140757 A1 | 5/2014 | Jimenez et al. | |
| 2014/0156007 A1* | 6/2014 | Pabst | A61F 2/442 623/17.16 |
| 2014/0194991 A1* | 7/2014 | Jimenez | A61F 2/442 623/17.15 |
| 2014/0236296 A1* | 8/2014 | Wagner | A61F 2/447 623/17.15 |
| 2014/0249629 A1* | 9/2014 | Moskowitz | A61B 17/0642 623/17.15 |
| 2014/0343608 A1 | 11/2014 | Whiton et al. | |
| 2015/0088258 A1 | 3/2015 | Jimenez et al. | |
| 2015/0100128 A1* | 4/2015 | Glerum | A61F 2/447 623/17.16 |
| 2015/0148908 A1* | 5/2015 | Marino | A61F 2/4455 623/17.16 |
| 2015/0272743 A1* | 10/2015 | Jimenez | A61F 2/447 623/17.16 |
| 2015/0272745 A1 | 10/2015 | Jimenez et al. | |
| 2015/0272746 A1 | 10/2015 | Jimenez et al. | |
| 2015/0351925 A1* | 12/2015 | Emerick | A61F 2/447 623/17.16 |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008-208932 A | 9/2008 |
| WO | WO 2004/026188 A2 | 4/2004 |
| WO | WO 2004/109155 A1 | 12/2004 |
| WO | WO 2005/081330 A2 | 9/2005 |
| WO | WO 2005/096975 A2 | 10/2005 |
| WO | WO 2006/094535 A1 | 9/2006 |
| WO | WO 2006/116052 A2 | 11/2006 |
| WO | WO 2006/125329 A1 | 11/2006 |
| WO | WO 2007/002583 A2 | 1/2007 |
| WO | WO 2007/009107 A2 | 1/2007 |
| WO | WO 2007/028140 A2 | 3/2007 |
| WO | WO 2007/076377 A2 | 7/2007 |
| WO | WO 2007/111979 A2 | 10/2007 |
| WO | WO 2008/137192 A1 | 11/2008 |

(56) References Cited

FOREIGN PATENT DOCUMENTS

| WO | WO 2009/018349 A2 | 2/2009 |
|---|---|---|
| WO | WO 2010/078468 A2 | 7/2010 |
| WO | WO 2010/078520 A2 | 7/2010 |

OTHER PUBLICATIONS

Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.

Printout from Video for OmniLIF Features from Lumber Jax; https://seelio.com/w/fgf/omnilif-the-new-standard-in-spinal-deformity-correction-and-fusion?student=lumbarjax; dated Nov. 27, 2014, 11 pages.

PCT/US2010/042941, filed Jul. 22, 2010, International Search Report and Written Opinion, dated Apr. 25, 2011.

PCT/US2010/042915, filed Jul. 22, 2010, Search Report and Written Opinion dated Apr. 22, 2011.

PCT/US2009/069876, filed Dec. 30, 2009, International Search Report and Written Opinion dated Sep. 27, 2010, 10 pages.

PCT/US2009/069958, filed Dec. 31, 2009, International Search Report and Written Opinion dated Nov. 29, 2010, 7 pages.

PCT/US2015/055449, filed Oct. 14, 2015, International Search Report and Written Opinion dated Dec. 11, 2015, 9 pages.

PCT/US2015/032977, filed May 28, 2015, International Search Report and Written Opinion dated Sep. 21, 2015, 10 pages.

European Application No. EP 09837185, European Search Report dated May 14, 2013, 7 pages.

Japanese Application No. 2012-521784, JP Office Action dated Feb. 18, 2014, 8 pages.

PCT/US2013/067070, PCT Written Opinion/Search Report dated Feb. 27, 2014, 14 pages.

PCT/US2014/052913, PCT Written Opinion/Search Report dated Dec. 22, 2014, 10 pages.

Wenzel Spine, Inc., VariLift®-L Expandable Interbody Fusion Device: A proven solution for stand-alone fusion, Product Overview, 12 pages, 2010.

Peter A. Halverson, et. al., Tension-based Multi-stable Compliant: Rolling-contact Elements, Department of Mechanical Engineering, Brigham Young University, Provo UT, USA 84602, 34 pages, 2007.

Just L. Herder, Force Directed Design of Laparoscopic Forceps, ASME Design Engineering Technical Conference, 8 pages, 1998.

Alexander H. Slocum, Fundamentals of Design, 2005.

W. Küsswetter, A Supplementary Instrumentation for Posterior Fusion of Spine in Scoliosis, Archives of Orthopedic Traumatic Surgery, 1980, 1 page.

Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.

Amelie Jeanneau, et. al., A Compliant Rolling Contact Joint and its Application in a 3-DOF Planar Parallel Mechanism with Kinematic Analysis, ASME, Design Engineering Technical Conferences, 9 pages, 2004.

Hunter et al., Overview of Medical Devices, Department of Radiology, University of Arizona, Aug. 2001, pp. 89-140, vol. 30, No. 4, ISSN: 0363-0188.

Medtronic Sofamor Danek USA, Inc., *CAPSTONE* Instrument Set Technique, http://www.mtortho.com/public/capstone.pdf , © 2005, 25 pages.

Medtronic, CAPSTONE PEEK Spinal System Surgical Technique, http://www.mtortho.com/public/capstone_peek_st.pdf, © 2009, 36 pages.

Application and File History for U.S. Appl. No. 12/407,608, filed Mar. 19, 2009, Inventors Jimenez et al.

Application and File History for U.S. Appl. No. 12/650,994 filed Dec. 31, 2009, Inventors Jimenez et al.

Application and File History for U.S. Appl. No. 12/651,266, filed Dec. 31, 2009, Inventors Jimenez et al.

Application and File History for U.S. Appl. No. 12/841,465, filed Jul. 22, 2010, now U.S. Pat. No. 8,303,663, Inventors Jimenez et al.

Application and File History for U.S. Appl. No. 12/841,869, filed Jul. 22, 2010, Inventors Jimenez et al.

Application and File History for U.S. Appl. No. 13/189,410, filed Jul. 22, 2011, Inventor Jimenez.

Application and File History for U.S. Appl. No. 13/661,534, filed Oct. 26, 2012, Inventor Jimenez.

Application and File History for U.S. Appl. No. 13/591,463, filed Aug. 22, 2012, Inventor Jimenez.

Application and File History for U.S. Appl. No. 13/891,356, filed May 10, 2013, Inventor Jimenez et al.

Application and File History for U.S. Appl. No. 14/024,764, filed Sep. 12, 2013, Inventor Jimenez et al.

Application and File History for U.S. Appl. No. 14/153,281, filed Jan. 13, 2014. Inventor Jimenez.

Application and File History for U.S. Appl. No. 14/563,660, filed Dec. 8, 2014. Inventor Jimenez et al.

Application and File History for U.S. Appl. No. 14/242,451, filed Apr. 1, 2014. Inventor Jimenez et al.

Application and File History for U.S. Appl. No. 14/318,196, filed Jun. 27, 2014. Inventor Jimenez et al.

Application and File History for U.S. Appl. No. 14/592,507, filed Jan. 8, 2015. Inventor Jimenez et al.

\* cited by examiner

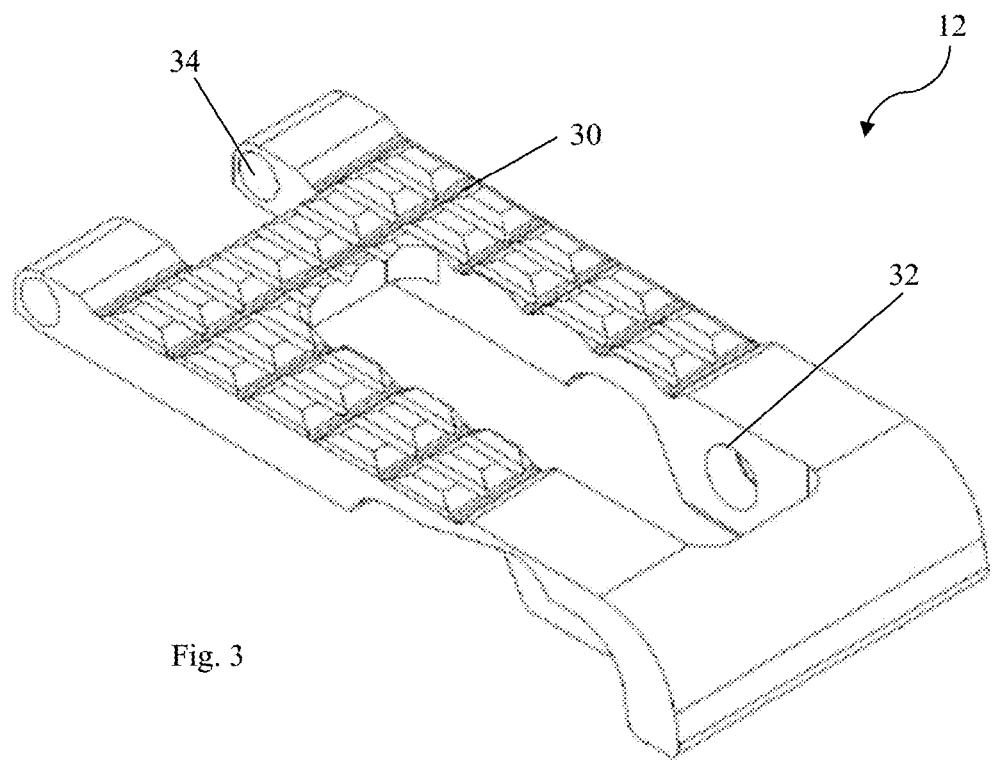
Fig. 3
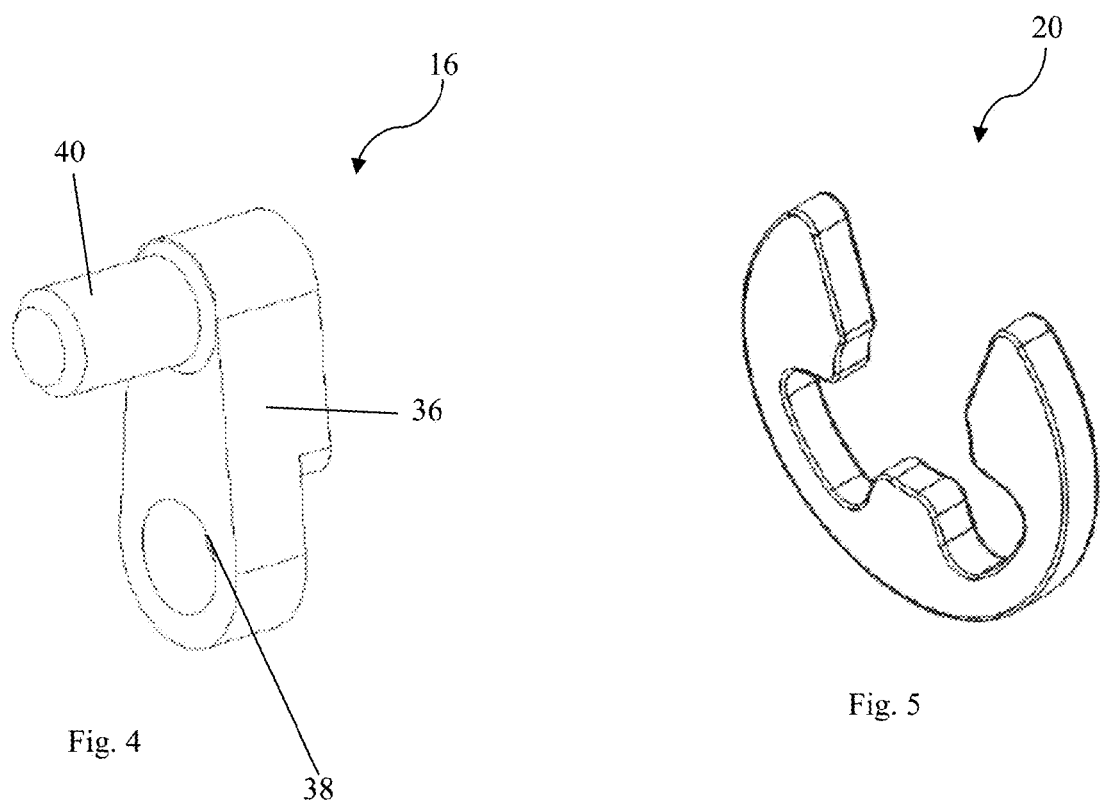
Fig. 4
Fig. 5

EXPANDABLE INTERVERTEBRAL CAGE

RELATED APPLICATIONS

The present application is a Continuation in Part of U.S. patent application Ser. No. 14/242,451 entitled "EXPANDABLE INTERVERTEBRAL CAGE", filed Apr. 1, 2014, which is incorporated herein by reference in its entirety. This application is also related to PCT Application No. PCT/US2014/052913 entitled "EXPANDABLE INTERVERTEBRAL CAGE," filed Aug. 27, 2014.

TECHNICAL FIELD

The present invention relates to the distraction and fusion of vertebral bodies. More specifically, the present invention relates to devices and associated methods for distraction and fusion of vertebral bodies that remain stable when implanted and facilitate fusion following their use for distraction to aid in the correction of spinal deformity by reducing a collapsed disc and establishing sagittal alignment, lordosis, or kyphosis.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allow load sharing to enhance bone formation and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

U.S. Pat. Nos. 7,070,598 and 7,087,055 to Lim et al. disclose minimally invasive devices for distracting the disc space. The devices include scissor-jack-like linkages that are used to distract a pair of endplates associated with adjacent vertebra from a first collapsed orientation to a second expanded orientation. A pull arm device is used to deliver and distract the device in the disc space. However, the device is primarily used for distraction and not subsequent vertebral fusion. The device would not work as a fusion device, because once the pull arm is disconnected from the device, the device will not be stable enough to maintain proper spacing of the vertebrae until fusion can occur. The endplates of the device are also solid and do not permit bone growth for successful fusion.

U.S. Patent Publication No. 2008/0114367 to Meyer discloses a device that uses a scissor-jack-like arrangement to distract a disc space. To solve the instability problem of the scissor-jack arrangement, a curable polymer is injected to fill the disc space and the distraction device is disabled from attempting to support the load. The curable polymer and disabling of the device are necessary because the device could not adequately support the distracted disc space. The base plates of the device have at least two or more degrees of freedom, collectively, in a distracted position and are therefore not stable under the loads encountered supporting the disc space. Absent injection of the polymer, and the support and control supplied by the implanting physician via the removable distraction tool, the base plates would collapse, which could cause severe damage to the vertebral bodies.

Accordingly, there is a need in the art for a device that can distract adjacent vertebral bodies in a minimally invasive manner while providing stable support for the disc space during fusion; particularly, a device that would allow for angular orientation of the base plates to be matched exactly to the unique alignment, or desired alignment, of a patient's spine.

SUMMARY OF THE DISCLOSURE

According to an embodiment, an expandable intervertebral cage device adapted to be implanted into an intervertebral disc space in a patient's body. The device includes a first base plate having a first outer bearing surface configured to interface with a first vertebra of the intervertebral disc space, a second base plate having a second outer bearing surface configured to interface with a second vertebra of the intervertebral disc space, a proximal block mechanically coupled to the first base plate and the second base plate, wherein the proximal block comprises internal threading, a distal block comprising an internal passage, and exactly two arm assemblies, wherein a first one of the two arm assemblies is arranged on a first side of the device and a second one of the two arm assemblies is arranged on a second side of the device, wherein each of the exactly two arm assemblies comprises a first arm mechanically coupled to the first base plate and the distal block and a second arm is mechanically coupled to the second base plate and the distal block. A screw is arranged partially within the internal threading of the proximal block and passing through the internal passage of the distal block, such that rotation of the screw relative to the proximal block causes a change in distance between the proximal block and the distal block, and a corresponding change in the spacing and lordosis of the device.

BRIEF DESCRIPTION OF THE DRAWINGS

The invention may be more completely understood in consideration of the following detailed description of various embodiments of the invention in connection with the accompanying drawings, in which:

FIG. 3 is a perspective view of an end plate, according to an embodiment.

FIG. 4 is a perspective view of a side arm, according to an embodiment.

FIG. 5 is a perspective view of a ring pin, according to an embodiment.

Figure 1A:
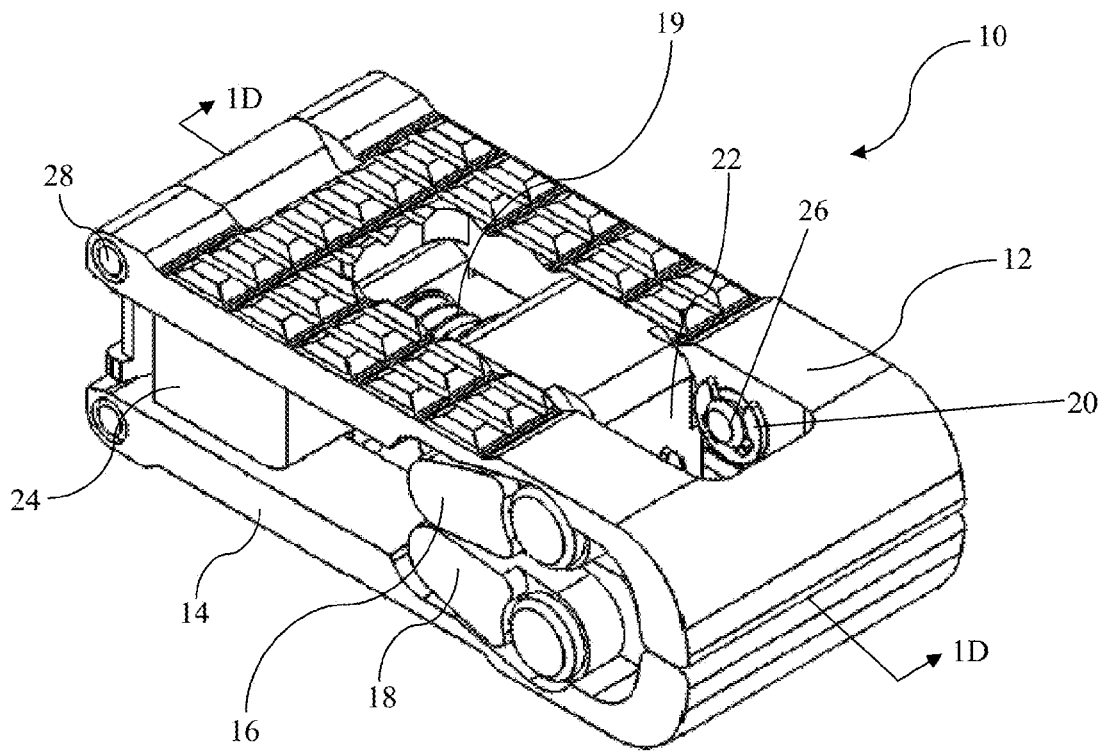
FIGS. 1A-1B are perspective views of an expandable intervertebral cage device according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention. U.S. Pat. No. 8,628,577, invented by the inventor of the present application, discloses a stable intervertebral body fusion and distraction device. This patent is hereby incorporated herein by reference in its entirety other than the summary of the invention, claims and any express definitions set forth therein.

Figure 1B:
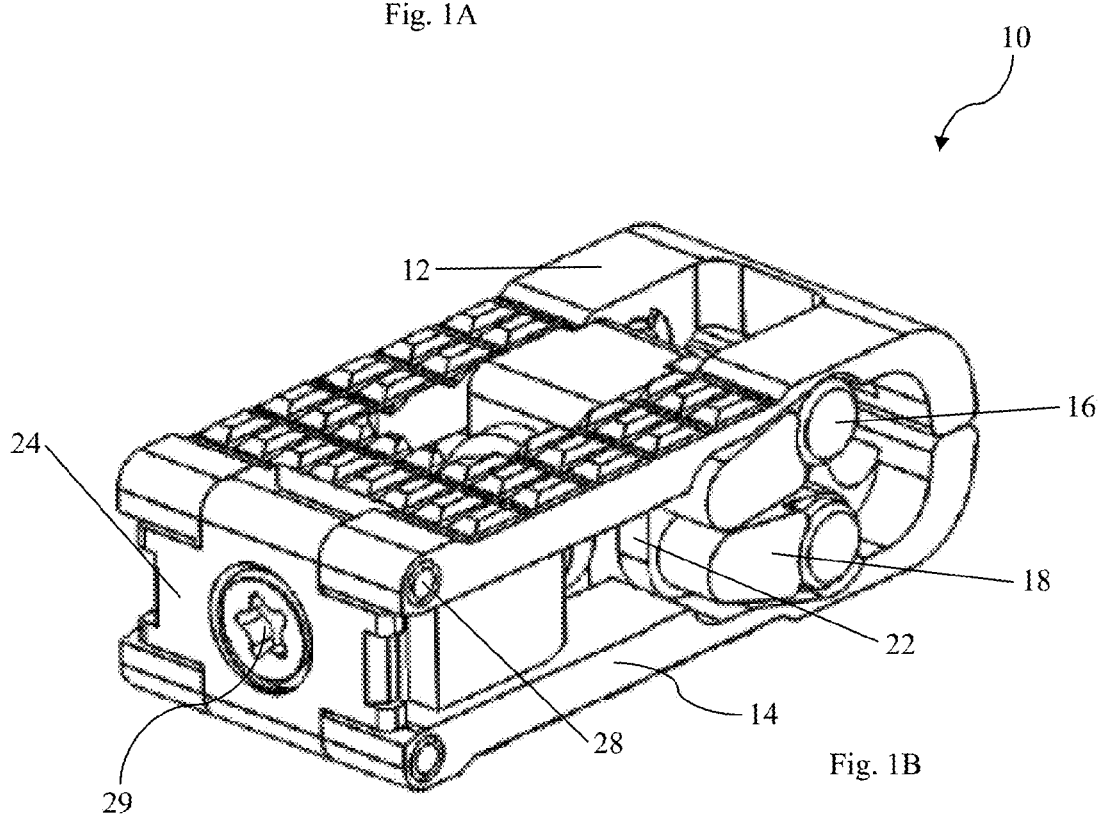
Figure 1C:
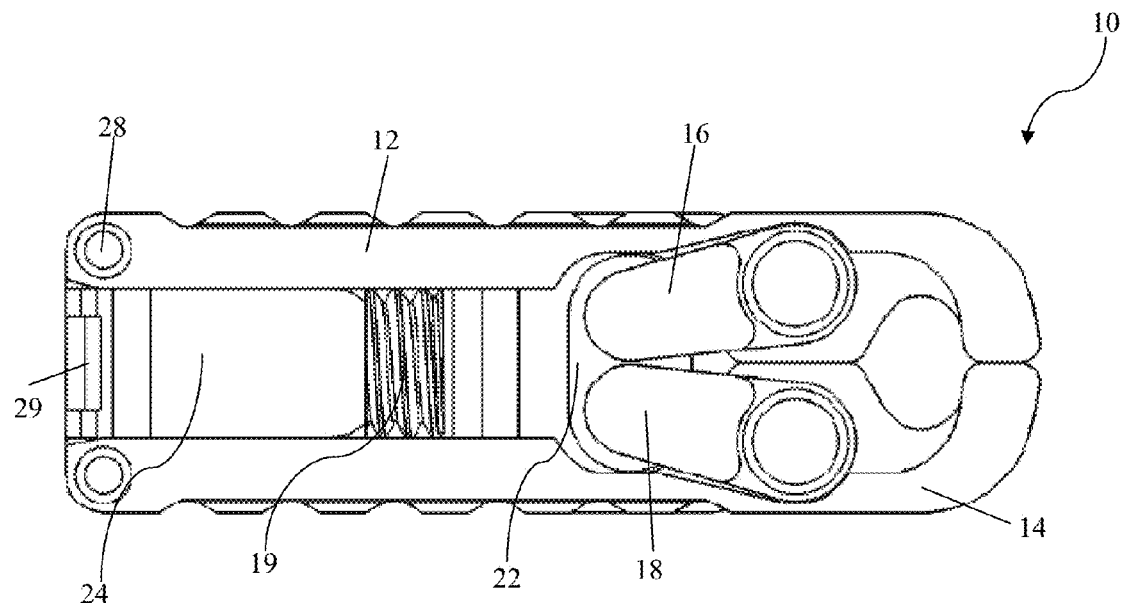
FIG. 1C is a side view of the expandable intervertebral cage device according to the embodiment of FIGS. 1A-1B.
Figure 1D:
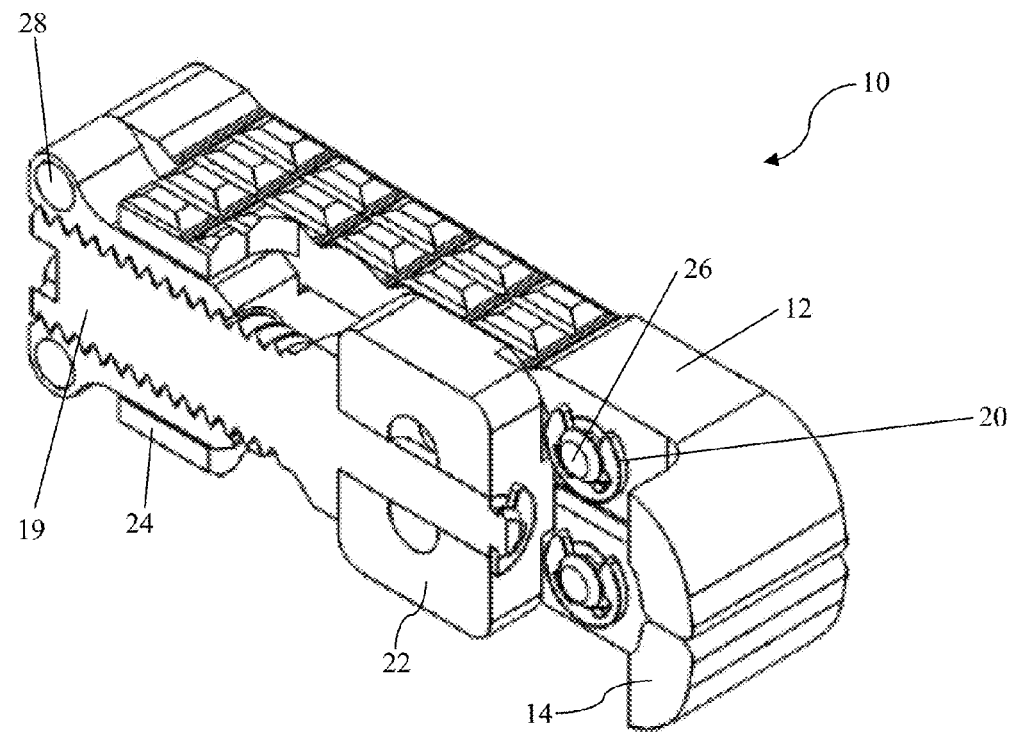
FIG. 1D is a cross-sectional view of the intervertebral cage device according to the embodiment of FIGS. 1A-1C, taken along line 1D-1D of FIG. 1A.

FIG. 1A is a perspective view of expandable intervertebral cage device 10, as seen from a distal end. FIG. 1B shows the same intervertebral cage device 10 from an opposite, proximal end. As shown in FIGS. 1A and 1B, intervertebral cage device 10 is in a collapsed position. FIG. 1C is a side view of the intervertebral cage device 10 in the collapsed position, and FIG. 1D is a cross-sectional view of the intervertebral cage device 10 taken across the cross-section line 1D-1D shown in FIG. 1A. FIGS. 2A-2D are counterparts to FIGS. 1A-1D showing the same intervertebral cage device 10. However, in FIGS. 2A-2D, while the views of intervertebral cage device 10 are the same as their respective counterparts in FIGS. 1A-1D, device 10 is in a fully expanded configuration rather than the collapsed position. FIGS. 3-9 depict individual elements or parts of device 10 in isolation and in more detail.

Intervertebral cage device 10 includes first base plate 12 and second base plate 14. On each side (i.e., each edge perpendicular to both the base plates 12 and 14 and the proximal/distal axis), intervertebral cage device 10 includes a first arm 16, second arm 18, screw 19, several rings 20, distal block 22, proximal block 24, pins 26, and rods 28. The hidden side of the device 10, not visible in the perspective views herein, comprises many substantially similar structures to those described with reference to the numbered elements. Intervertebral cage device 10 is a device that can be used to hold two structures, such as the vertebrae of a spine, in a fixed spatial relationship with respect to one another. As will be described with respect to subsequent figures, device 10 can be expanded to hold structures in any fixed spatial relationship with a range of distances and angles with respect to one another. Device 10 provides desirable spacing and lordosis and can be operated using a single screw, as described below, to achieve commonly used intervertebral spacing and lordosis levels. In contrast to the multiple-screw devices described above, the user of a single screw device reduces the complexity and increases the mechanical strength of the device. In some embodiments, at full extension the device 10 can exhibit about 23° of lordosis, for example, which is greater than a commonly used angle for many intervertebral devices.

As shown in more detail with respect to FIG. 3, first base plate 12, which is substantially similar to second base plate 14, comprises textured surface 30, arm socket 32, and rod passage 34. First base plate 12 is a portion of device 10 that comprises a bearing surface. As used throughout this disclosure, "bearing surface" refers to the outside surface of a base plate (e.g., 12, 14) that interfaces with the endplate of a vertebra, other bone, or other structures that are to be held in a fixed spatial relationship from one another. Textured surface 30 can comprise, for example, any texture that promotes bone growth to hold the base plate 12, or which provides grip or traction when compressed against bone. Arm socket 32 is usable to provide a mechanical connection between base plate 12 and a corresponding structure, such as first arm 16, as depicted in FIGS. 1A-1D and 2A-2D. Similarly, rod passage 34 can be used to facilitate a mechanical connection between base plate 12 and a corresponding structure, such as proximal block 24, as described in more detail below.

As shown in FIGS. 1A-1D and 2A-2D, base plates 12 and 14 are arranged on opposite from one another in device 10, and can be positioned within a range of distances and angles relative to one another, depending on the extent of the expansion of device 10. For example, as shown with respect to FIGS. 1A-1D, the device 10 is in a collapsed position, and base plates 12 and 14 are relatively close to one another, and arranged substantially parallel to one another. In the configuration shown with respect to FIGS. 2A-2D, the base plates 12 and 14 are relatively further away from one another on the distal end, and are angled relative to one another (this angle is sometimes referred to as lordosis). In embodiments, the extent of lordosis and/or distance between various parts of the base plates 12 and 14 can vary. In some embodiments, base plates can each be angled at 23 degrees. In this embodiment, a proximal end of each base plate can remain at a generally constant distance from each other as the device is expanded about pins 28 (with perhaps a slight change in distance as the plates rotate about pins).

Referring now to FIG. 4, the mechanism by which device 10 is expanded or collapsed is shown, and in particular first arm 16. First arm 16, which is substantially similar to second arm 18, includes body portion 36, first connector 38, and second connector 40. A substantially similar pair of arms to first arm 16 and second arm 18 are included in device 10 on the side that is not depicted in the perspective views previously shown. Body portion 36 extends between first connector 38 and second connector 40. The distance between first connector 38 and second connector 40 determines in part the extent to which the base plates 12 and 14 of FIGS. 2A-2D can be distanced from one another, and the angle between them. First connector 38 and second connector 40 can each be rotatably connected to an adjoining structure. So, for example, as shown with respect to FIGS. 1A-1D and 2A-2D, first connector 38 can be connected to first plate 12 or second plate 14 via a pin 26. Likewise, second connector 40 can be connected to distal block 22. The connections space the parts from one another, while allowing relative rotation between them.

Referring now to FIG. 5, ring 20 is depicted, which can also support interconnection between the base plate 12 and the distal block 22 via any of the arms. In particular, ring 20 holds pin 26 (shown in more detail with respect to FIG. 8) such that it passes through both first base plate 12 and first connector 38 of first arm 16. In operation, the effects of lateral forces (i.e., forces perpendicular to the proximal-distal directions previously described) are mitigated by ring 20. Ring 20 can prevent some types of relative lateral movement between first base plate 12, first arm 16, and pin 26. Ring 20 does this by snapping into groove 52 of pin 26, as described in more detail with respect to FIG. 8.

Figure 6:
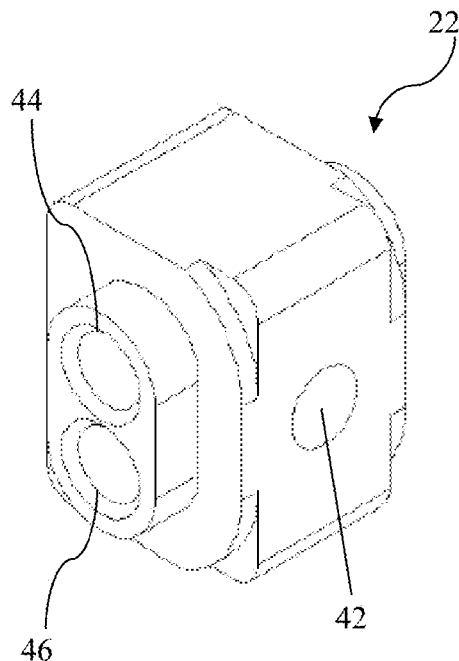
FIG. 6 is a perspective view of a proximal block, according to an embodiment.

Referring now to FIG. 6, distal block 22 is shown in perspective. Distal block 22 includes internal passage 42, first bearing 44, and second bearing 46. Internal passage 42 is configured to provide a passage for a portion of screw 19, as shown previously with respect to FIG. 1D and FIG. 2D. In some embodiments, the portion of screw 19 that passes through internal passage 42 is a shank (i.e., unthreaded), or else the internal passage 42 itself is unthreaded, or both, such that there is not co-rotation between distal block 22 and screw 19. Screw 19 passes through internal passage 42 in the embodiment shown in FIGS. 1A-1D and 2A-2D, and as such the distal block 22 and screw 19 are fixed relative to one another in the proximal/distal directions. As described in more detail below with respect to FIG. 7, rotation of screw 19 can cause screw 19 to advance in either the proximal or distal direction, which thereby causes a corresponding movement of the distal block 22 in the same direction. As can be seen in the figures, screw 19 can define a first diameter at proximal block that is greater than a second diameter at distal block. The diameter of screw at the interface with distal block can be the same or greater than that at proximal block to prevent the screw from advancing distally through distal block. A ring 20 can prevent the screw 19 from being pulled proximally through the distal block.

First bearing 44 and second bearing 46 can receive a portion of another object, such as first arm 16 and second arm 18 as shown in FIGS. 1A-1D and 2A-2D. First arm 16 and/or second arm 16 can rotate relative to first bearing 44 and/or second bearing 46, while remaining mechanically fixed to one another. As described above, rotation of screw 19 can cause movement of distal block 22 in the proximal or distal direction. This results in corresponding displacement of the second connector 40 of the first arm 16 (and the corresponding structure in the second arm 18).

Figure 2A:
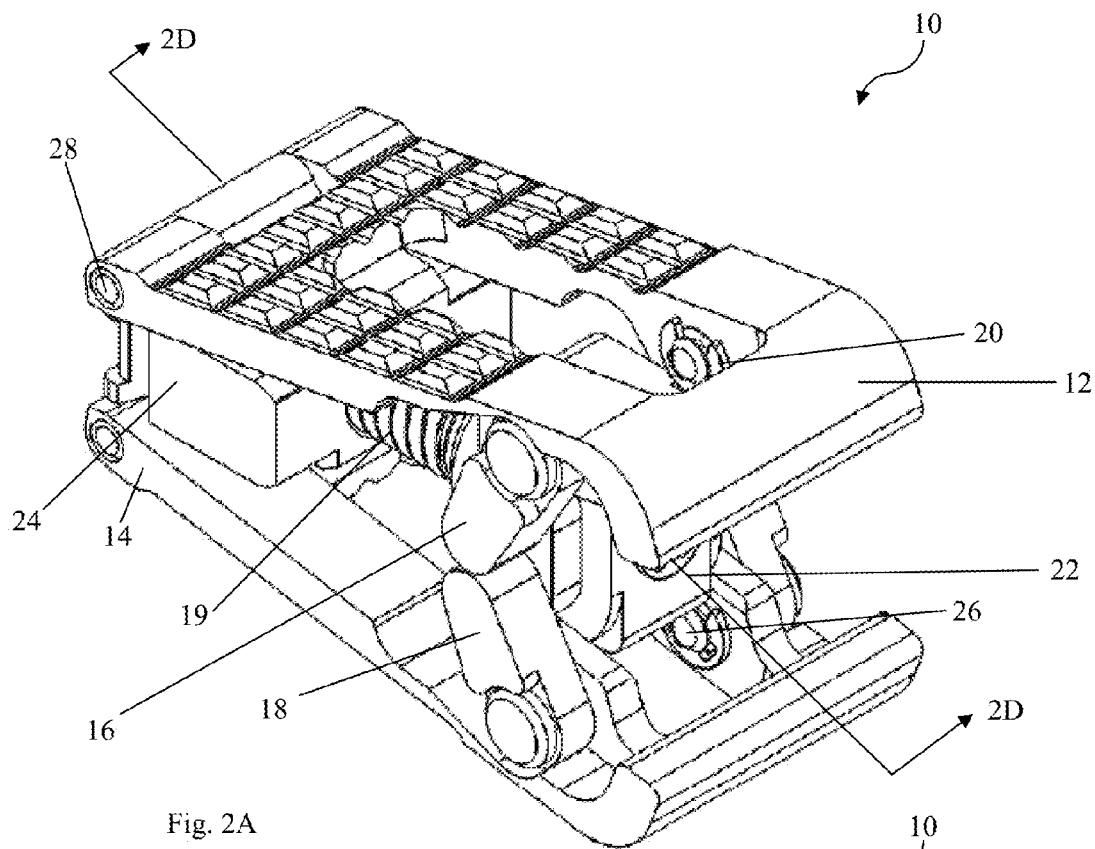
FIGS. 2A-2B are perspective views of an expanded intervertebral cage device according to an embodiment.
Figure 2B:
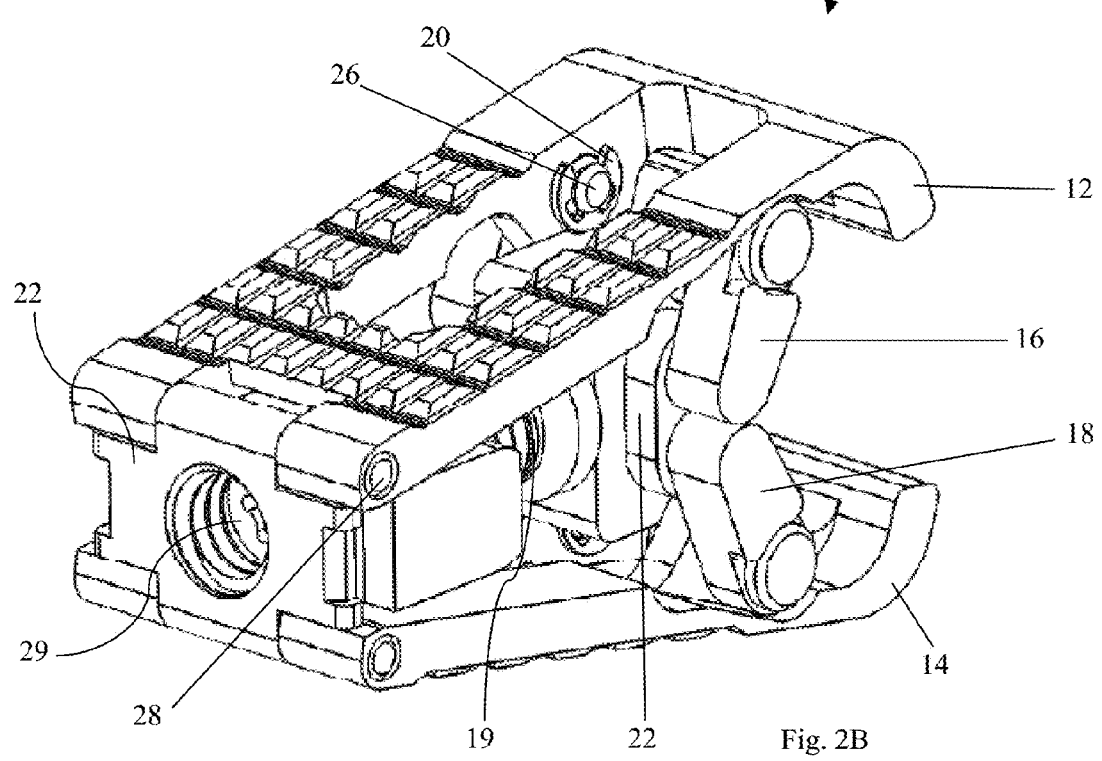
Figure 2C:
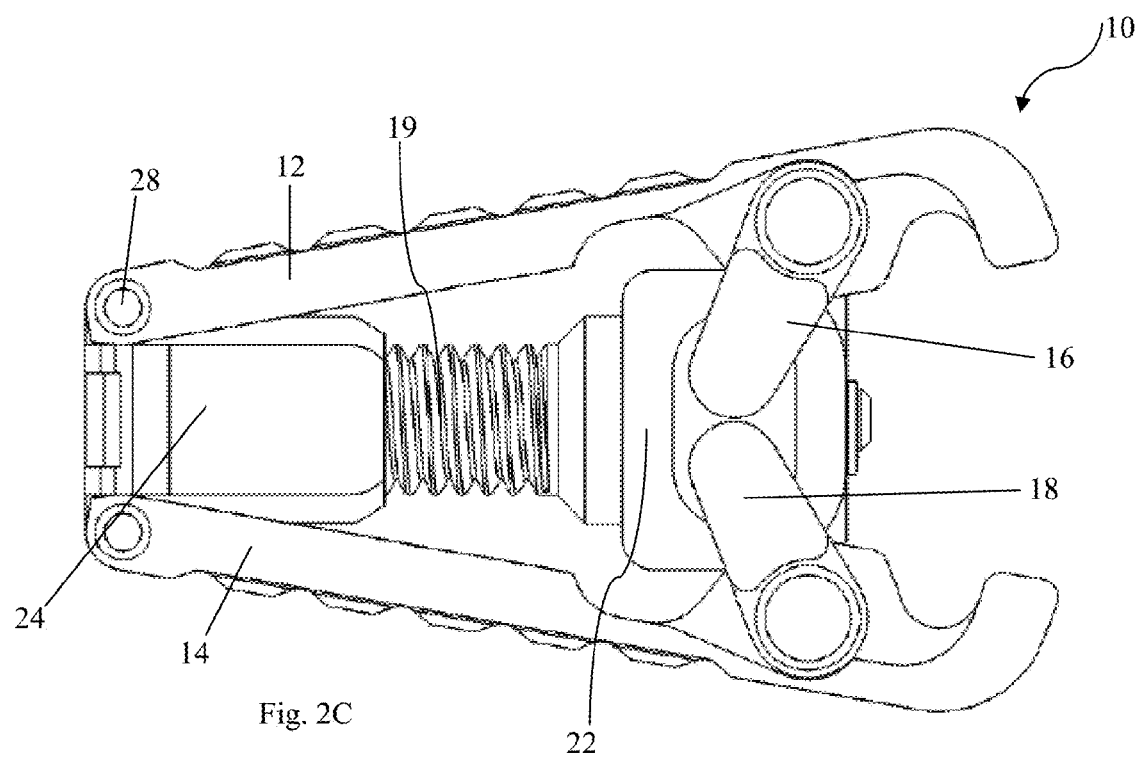
FIG. 2C is a side view of the expanded intervertebral cage device of FIGS. 2A-2B.
Figure 2D:
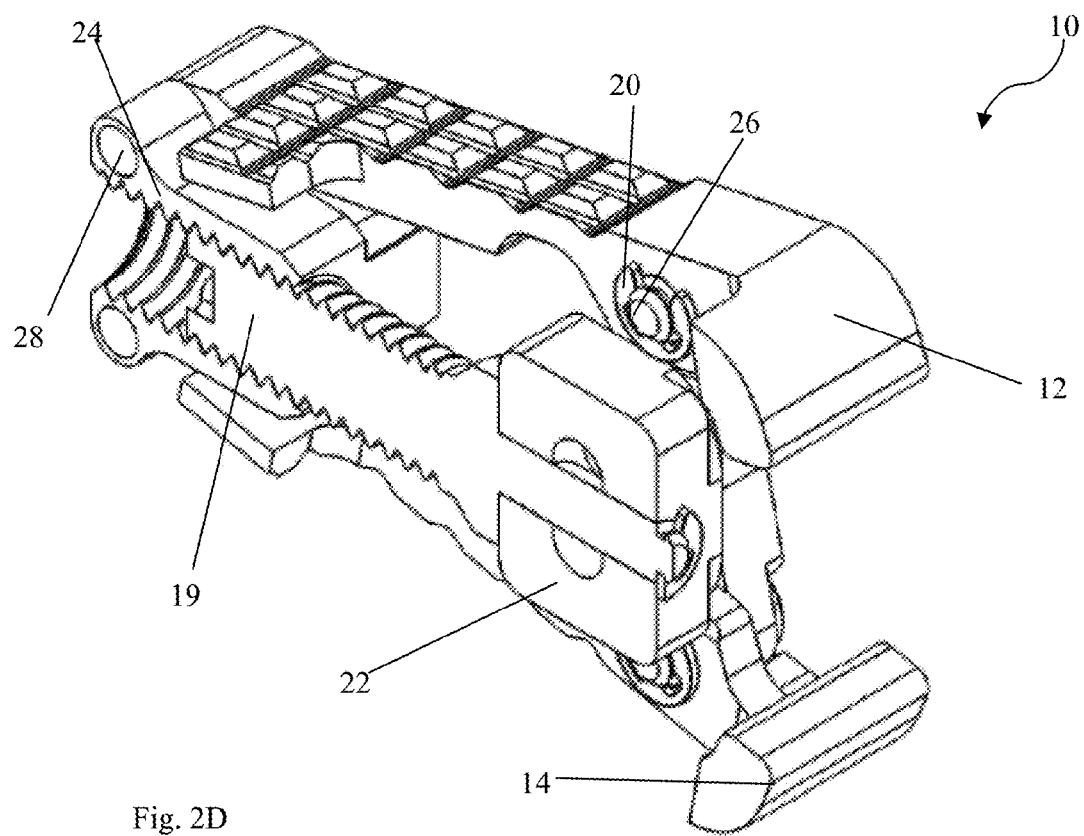
FIG. 2D is a cross-sectional view of the intervertebral cage device according to the embodiment of FIGS. 2A-2C, taken along line 2D-2D of FIG. 2A.
Figure 7:
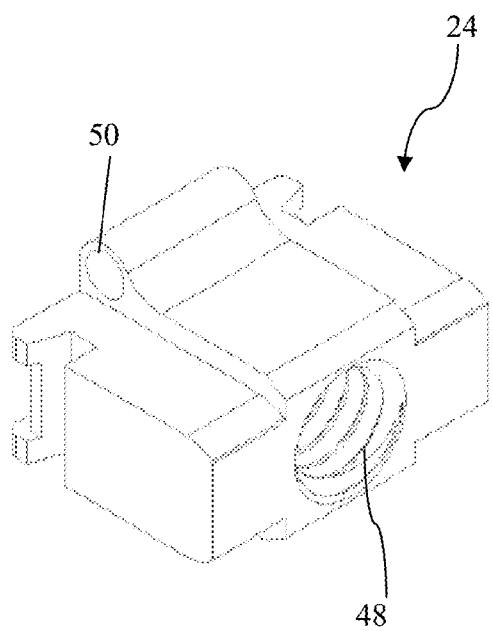
FIG. 7 is a perspective view of a distal block, according to an embodiment.

FIG. 7 is a perspective depiction of proximal block 24. Proximal block 24 includes internal threads 48 and rod passage 50. Internal threads 48 can be configured to interact with an adjacent component, such as screw 19 as shown in FIGS. 1D and 2D. Proximal block 24 is connected to first base plate 12 and second base plate 14 by rods 28. As shown in FIGS. 1A-1D and 2A-2D, rod 28 connects first base plate 12 with proximal block 24. Rod 28 can pass through rod passages 50 and 34 so that the proximal block 24 is mechanically coupled to first base plate 12 while allowing the base plates (12, 14) to rotate relative to the blocks (22, 24).

Figure 8:
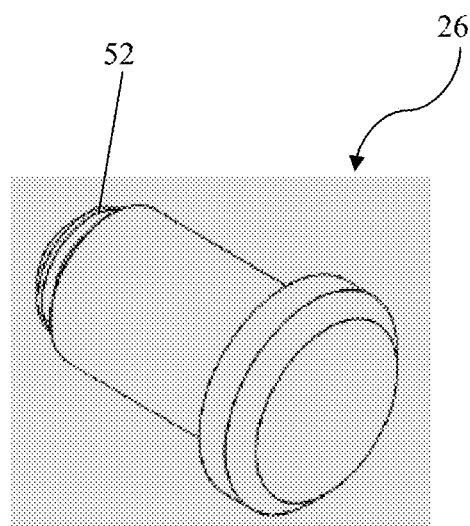
FIG. 8 is a perspective view of a pin, according to an embodiment.
Figure 9:
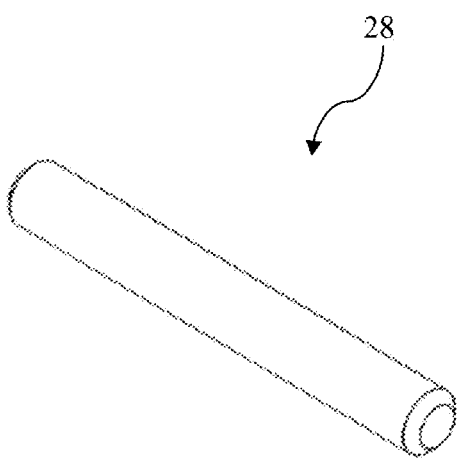
FIG. 9 is a perspective view of a rod, according to an embodiment.

FIGS. 8 and 9 depict the connection structures between the first base plate 12 and adjoining structures. In particular, FIG. 8 depicts a pin 26 that connects the first base plate 12 to the distal block 22 via the arms, and FIG. 9 depicts a rod 28 that connects the first base plate 12 to the proximal block 24. Pin 26 further includes groove 52 which can hold ring 20, as previously described.

In operation, first arm 16 and second arm 18 are rotatable and are connected to first base plate 12 and second base plate 14, respectively. Because the structural connection between first base plate 12 and screw 19 is substantially similar to the structural connection between second base plate 14 and screw 19, only the former will be described herein in detail. First base plate 12 is mechanically coupled via pins 26 to first arm 16 via arm socket 32. First arm 16 and second arm 18 are also each mechanically coupled to screw 19 through distal block 22. In all, this connection permits for first base plate 12 to be indirectly connected to the screw 19 while still permitting relative rotation between them. Together with rings 20, distal block 22, proximal block 24, and pins 26, a mechanical interconnection is formed between each of the base plates 12 and 14 that can be adjusted by an external tool (not shown). Rods 28 provide a pivot point that results in a specific relationship between the amount of extension of the device 10 and a relative angle between the first base plate 12 and the second base plate 14.

An external tool (not shown) can be used to turn screw 19, via head 29. Because proximal block 24 is internally threaded (as shown in more detail with respect to FIG. 7), rotation of screw 19 causes relative movement of the screw 19 with respect to the proximal block 24. By contrast, distal block 22 is not internally threaded. Rather, distal block 22 and screw 19 are connected such that movement of screw 19 in either the proximal or distal directions (i.e., the direction in which screw 19 moves relative to proximal block 24 when rotated) causes a corresponding movement of the distal block 22. This can be accomplished as shown, for example, in FIG. 2D, where distal block 22 is pushed and/or pulled by screw 19, and the interconnection is made by a spring or clamp on one side holding the distal block 22 against a flange on the screw 19. In alternative embodiments, various other interconnections between the screw and block can be made, which will result in co-movement in the proximal or distal direction without co-rotation. As distal block 22 is moved by screw 19, it forces movement of first arm 16 and second arm 18.

As screw 19 is rotated, due to the internal threading of proximal block 24, the distance between the distal block 22 and proximal block 24 changes. As the distance between distal block 22 and proximal block 24 increases, the arms 16 and 18 are caused to rotate. First arm 16 and second arm 18 rotate as the device 10 is converted from a collapsed configuration, such as that shown in FIGS. 1A-1D, to an expanded configuration, such as that shown with respect to FIGS. 2A-2D. This rotation results in increased distance between the first base plate 12 and the second base plate 14, as well as increased lordosis. As described with respect to other embodiments below, rotating screw 19 to change the distance between first base plate 12 and second base plate 14, as well as changing the amount of lordosis, can be useful to provide intervertebral support.

The embodiment shown in FIGS. 1A-1D, 2A-2D, and 3-9 provides such intervertebral spacing, support, and lordosis with a relatively straightforward mechanical structure. The device 10 can be implanted in a compact configuration, then expanded to the appropriate size and angle by rotating screw 19, causing the changes in angle and spacing previously described, as desired.

Figure 21A:
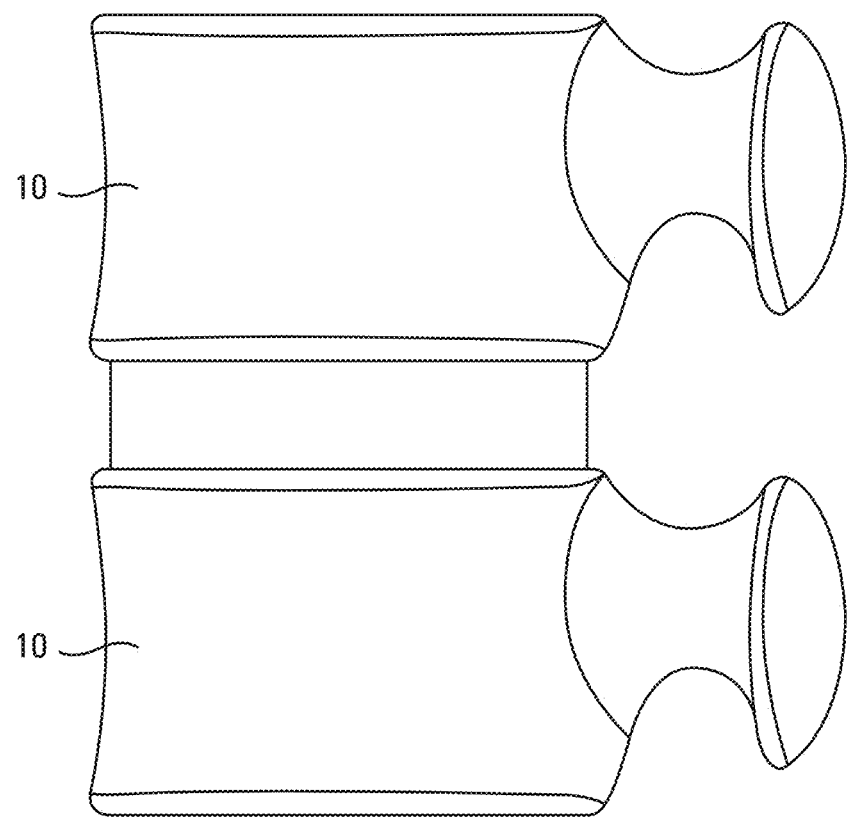
FIGS. 21A-21B are schematic representations of a pair of adjacent vertebral bodies.
Figure 21B:
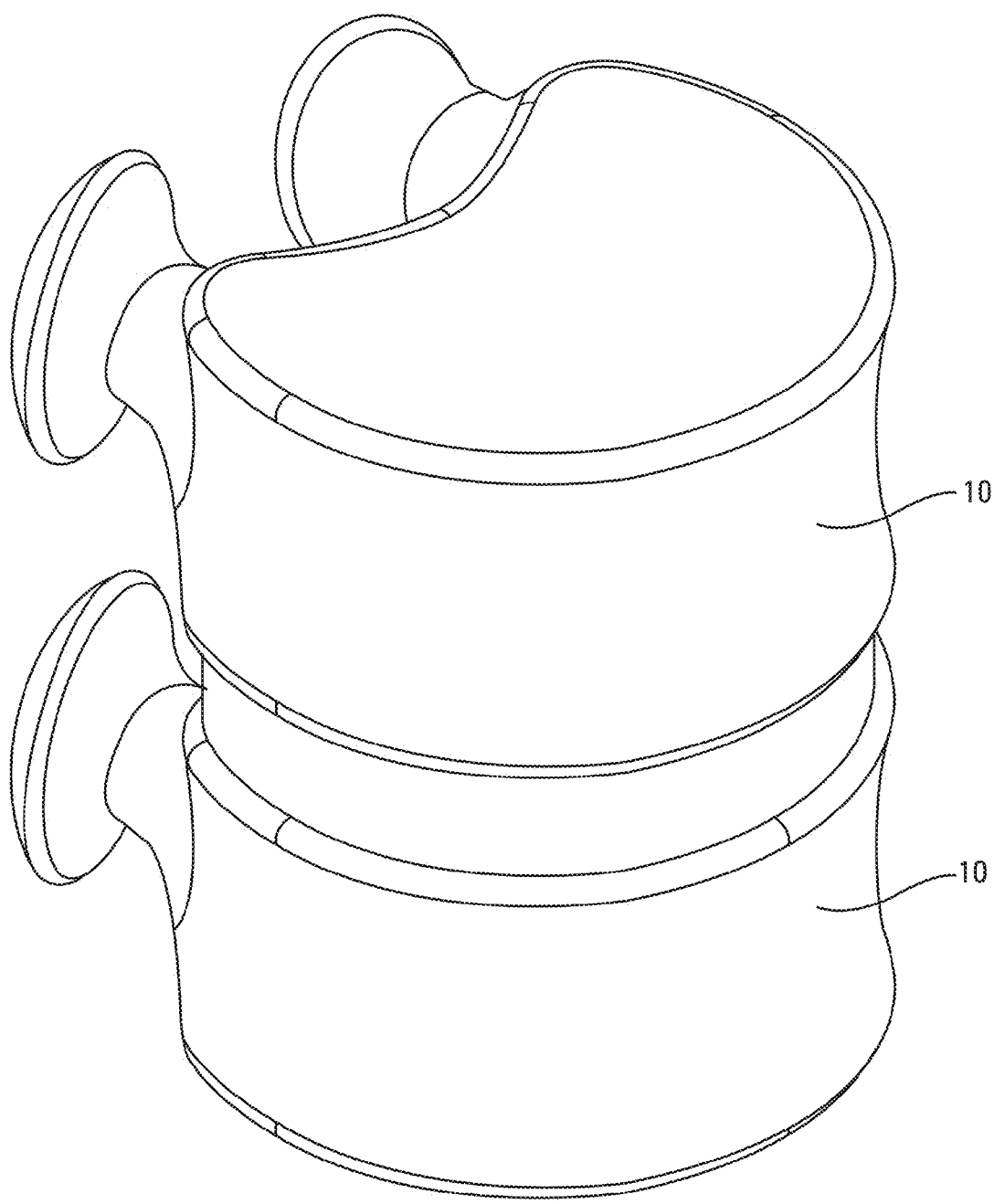

Referring to FIGS. 10A-10C and FIG. 11, there can be seen an expandable intervertebral cage device 100 according to an aspect of the present invention. Device 100 includes a device body 102. Device body 102 can include a nose portion 104, a rear portion 106, a pair of opposed base plates 108 having outer bearing surfaces 107, and a plurality of arm assemblies 110. Schematic representations of a pair of adjacent vertebral bodies 10 are depicted in FIGS. 21A-21B. Each arm assembly 110 can include a pair of opposed arms 112 hingedly attached to each other, with each opposing arm 112 hingedly attached to one of the base plates 108. In one embodiment, device 100 can include three arm assemblies 110a, 110b, and 110c, extending crosswise from first side 116 of device 100 to second side 118 of device 100. In one embodiment, opposing arms 112 of arm assemblies 110a, 110b, and 110c are pivotally coupled to a blocks 122a, 122b, and 122c with pins 114. Block 122a can be positioned nearest the rear portion 106, block 122c can be positioned nearest the nose portion 104, and block 122b can be positioned between blocks 122a and 122c.

Figure 12A:
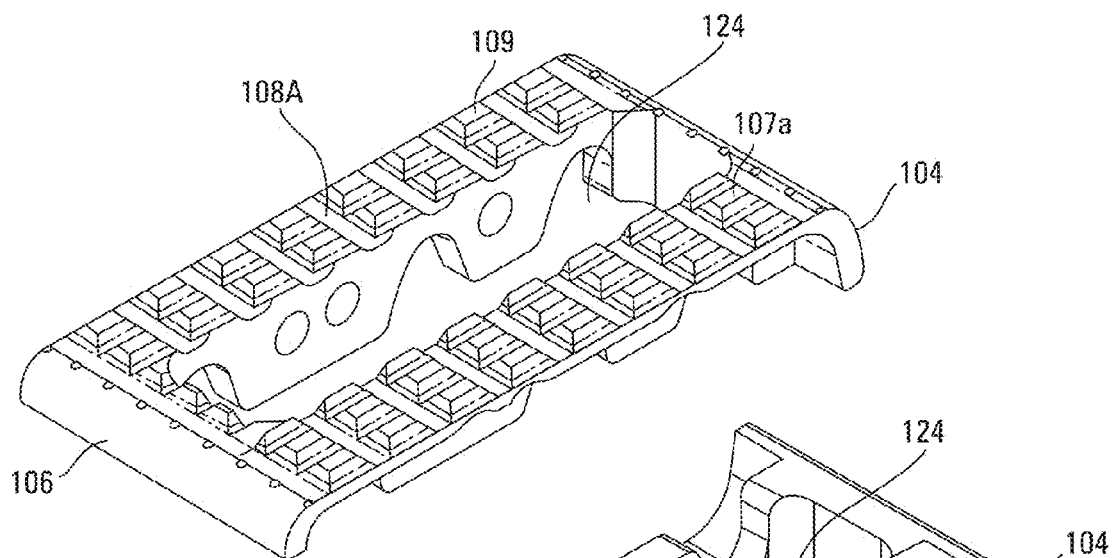
FIG. 12A is a perspective view of an embodiment of a first base plate according to an aspect of the present invention.
Figure 12B:
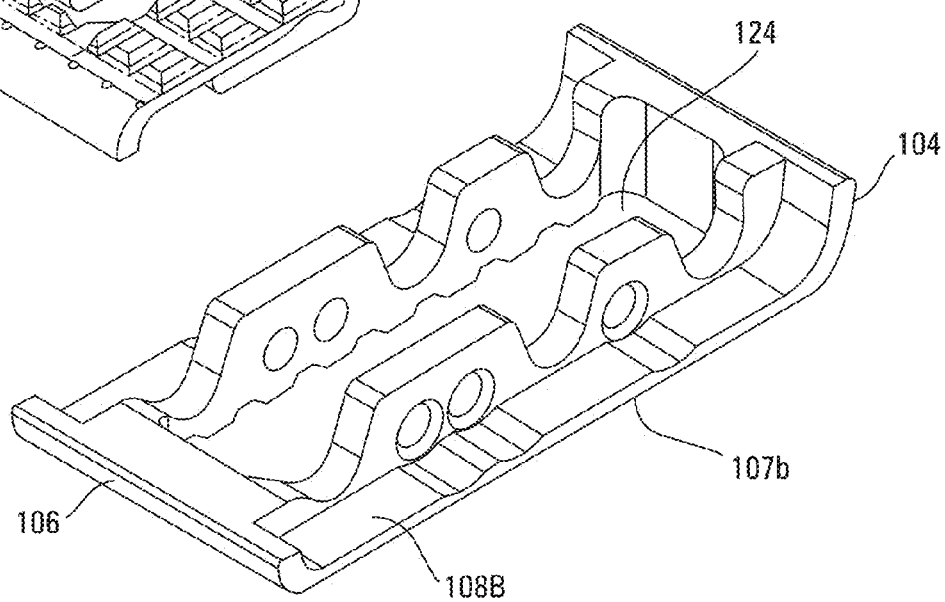
FIG. 12B is a perspective view of an embodiment of a second base plate according to an aspect of the present invention.
Figure 12C:
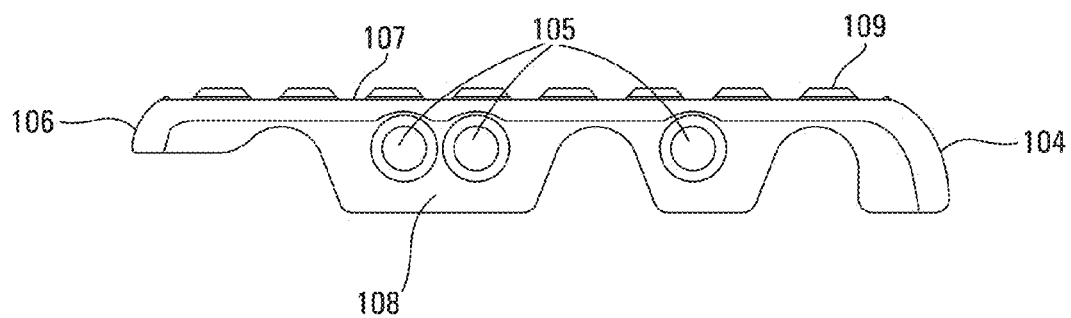
FIG. 12C is a side view of an embodiment of a base plate according to an aspect of the present invention.

Referring to FIGS. 12A-12C, in one embodiment, base plates 108 can include a first, or top, base plate 108a, with a top bearing surface 107a configured to interface with an end plate of a superior vertebra of the intervertebral disc space, and a second, or bottom, base plate 108b having a bottom bearing surface 107b configured to interface with an end plate of an inferior vertebra of the intervertebral disc space. In one embodiment, each base plate 108 can include one or more openings 124 to facilitate bone growth through the device 100. Openings 124 promote vertebral fusion because bone can grow directly through the device 100. Although depicted as being generally rectangular, opening 124 can comprise any shape. Alternatively, a generally solid surface or a surface with multiple openings can be provided on each base plate 108.

Base plates 108 can have a rough surface or teeth 109 to create friction with the base plates of the vertebra to prevent accidental extrusion of the device 100 or to promote bone growth for successful fusion. Base plates 108 or other elements of the device can also in some embodiments be made compliant for exaggerated non-uniform distraction while maintaining the stability of the device 100. Nose portion 104 can be tapered to facilitate insertion of the device 100 into the disc space. Rear portion 106 can also be tapered. In one embodiment, base plate 108 can include a plurality of bores 105. Each bore 105 can be sized to accept a portion of opposing arm 112 to facilitate a hinged coupling.

Figure 13:
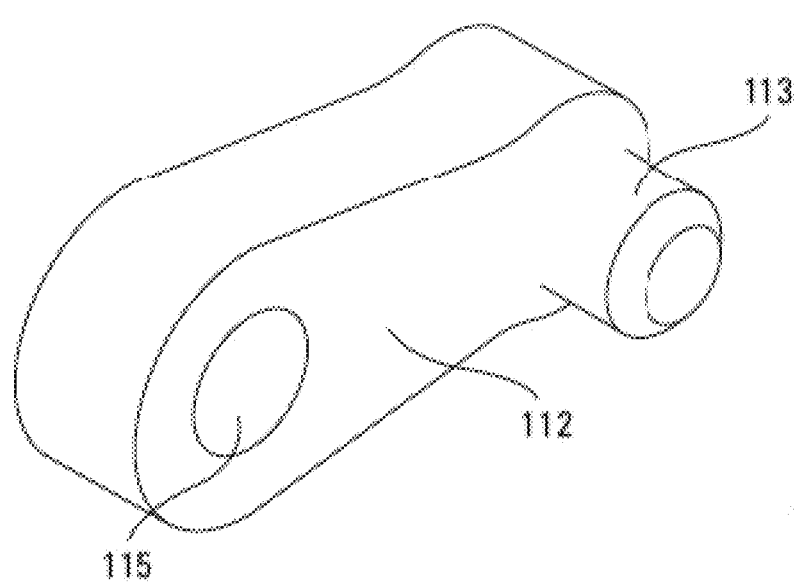
FIG. 13 is a perspective view of an embodiment of an arm according to an aspect of the present invention.

In one embodiment, device 100 can have a total of twelve arms 112 (four arms for each arm assembly 110a, 110b, and 110c, with two arms of each assembly on each side of the device). In one embodiment, all of the arms 112 can be substantially identical. Referring to FIG. 13, each arm 112 can include a protrusion 113 sized to fit into one of the bores 105 of base plate 108 to facilitate a hinged coupling. In one embodiment, arms 112 can be welded to base plates to prevent failure. Each arm 112 can include a bore 115 sized to accept a pin 114 for coupling the arm 112 to a block 122.

Figure 14:
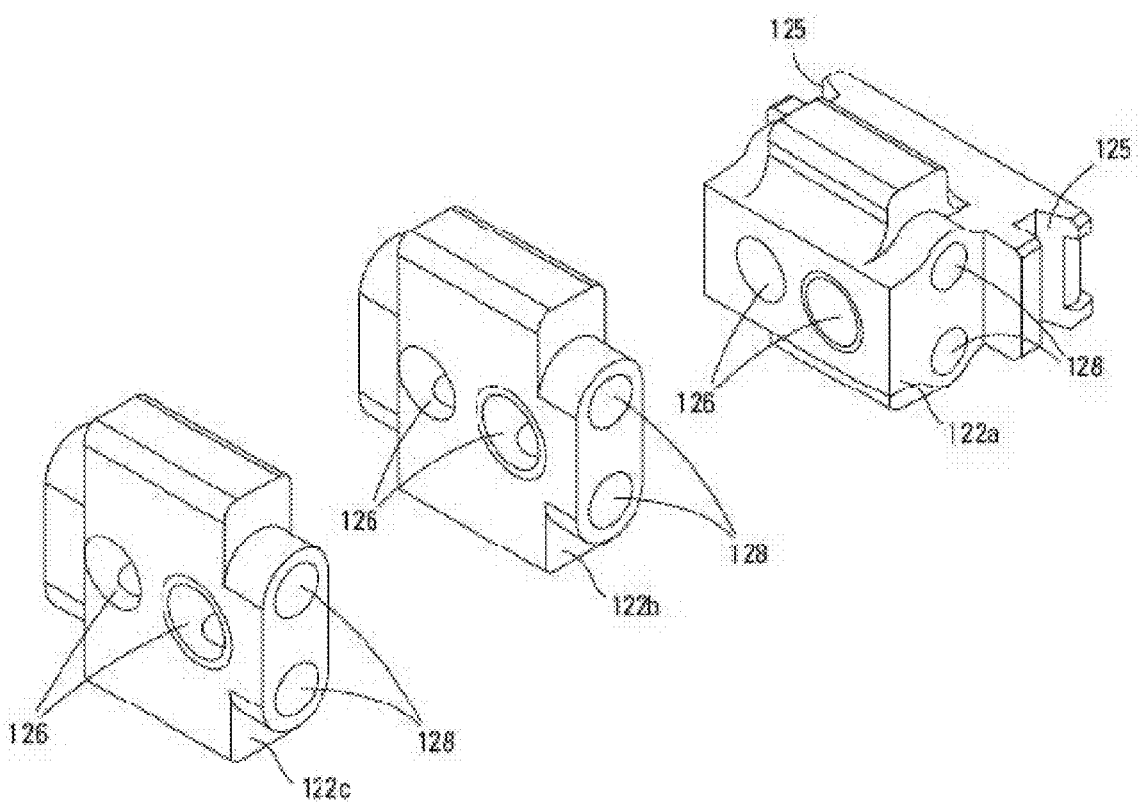
FIG. 14 is a perspective view of an embodiment of first, second and third blocks according to an aspect of the present invention.

In one embodiment, device can have a total of three blocks—a first or proximal block 122a, a second or central block 122b and a third or distal block 122c. Referring to FIG. 14, in one embodiment, central and distal blocks 122b and 122c can be substantially identical. Each block 122 can be defined by two side bores 128 sized to accept pin 114 for the purpose of coupling two arms 112 to block 122. In one embodiment, side bores 128 can be substantially parallel to one another. Each block 122 can also be defined by two longitudinal bores 126, each sized to accept an actuation member 120. In one embodiment, each longitudinal bore 126 can be threaded. In another embodiment, only one longitudinal bore 126 of each block 122 is threaded. In one embodiment, longitudinal bores 126 can be substantially parallel to one another. In one embodiment, longitudinal bores 126 can be orthogonal to side bores 128. Proximal block 122a can be adapted to attach to an insertion device for inserting device 100 into the disc space. In one embodiment, side slots 125 of proximal block 122a can be configured to receive portions of insertion device.

Figure 15:
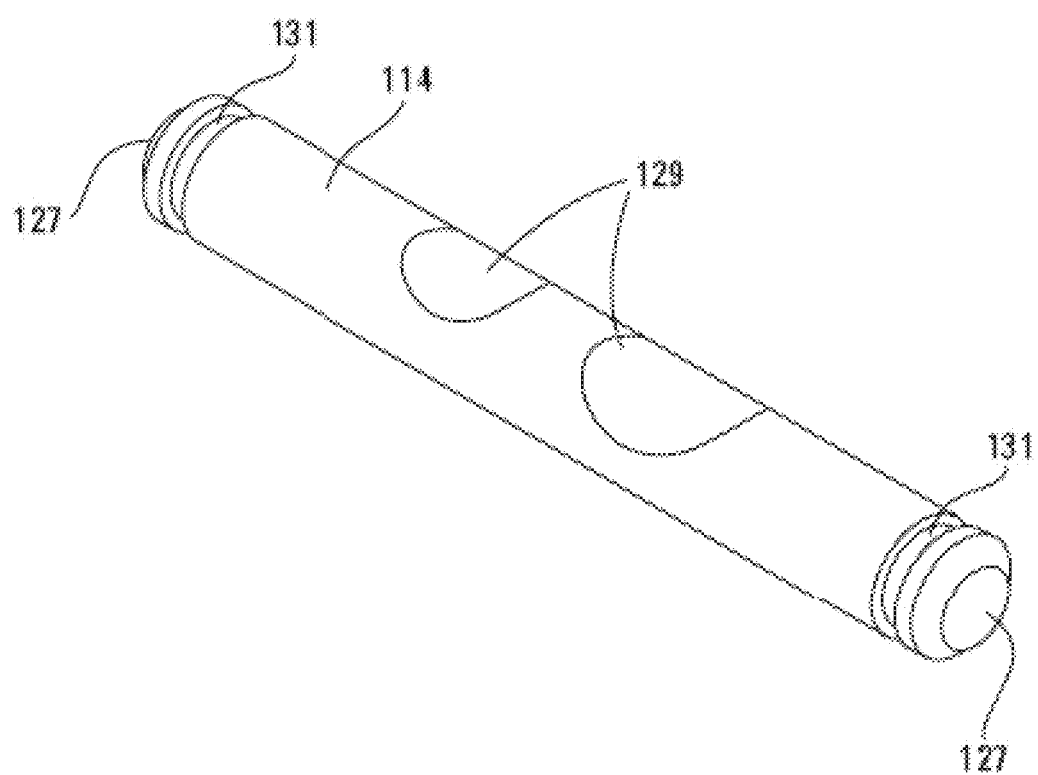
FIG. 15 is a perspective view of an embodiment of a pin according to an aspect of the present invention.

In one embodiment, device 100 can include a total of six pins 114. Referring to FIG. 15, each pin 114 can be substantially cylindrical in shape and have opposing ends 127 sized to fit into bore 115 of arms 112 on opposing sides 116, 118 of device 100. Pins can be sized to extend through side bore 128 of block 122 between opposing arms 112, for the purpose of pivotably coupling two arms 112 to a given block 122. In one embodiment, pin 114 can include notches 129. Notches 129 can be sized to allow clearance for actuation members 120 through longitudinal bores 126, thereby allowing each arm assembly 110 to be more compact. In one embodiment, pin 114 can include a slot 131 proximate each end 127 of pin 114 sized to accept a snap ring 133 (shown in FIG. 16) that sits outside of arms to lock pins in place. In one embodiment, a distal portion of one or more actuation members 120 can have a larger diameter than the remainder of actuation member. Longitudinal bores 126 would therefore be larger to accommodate this larger section of the screw.

Figure 16:
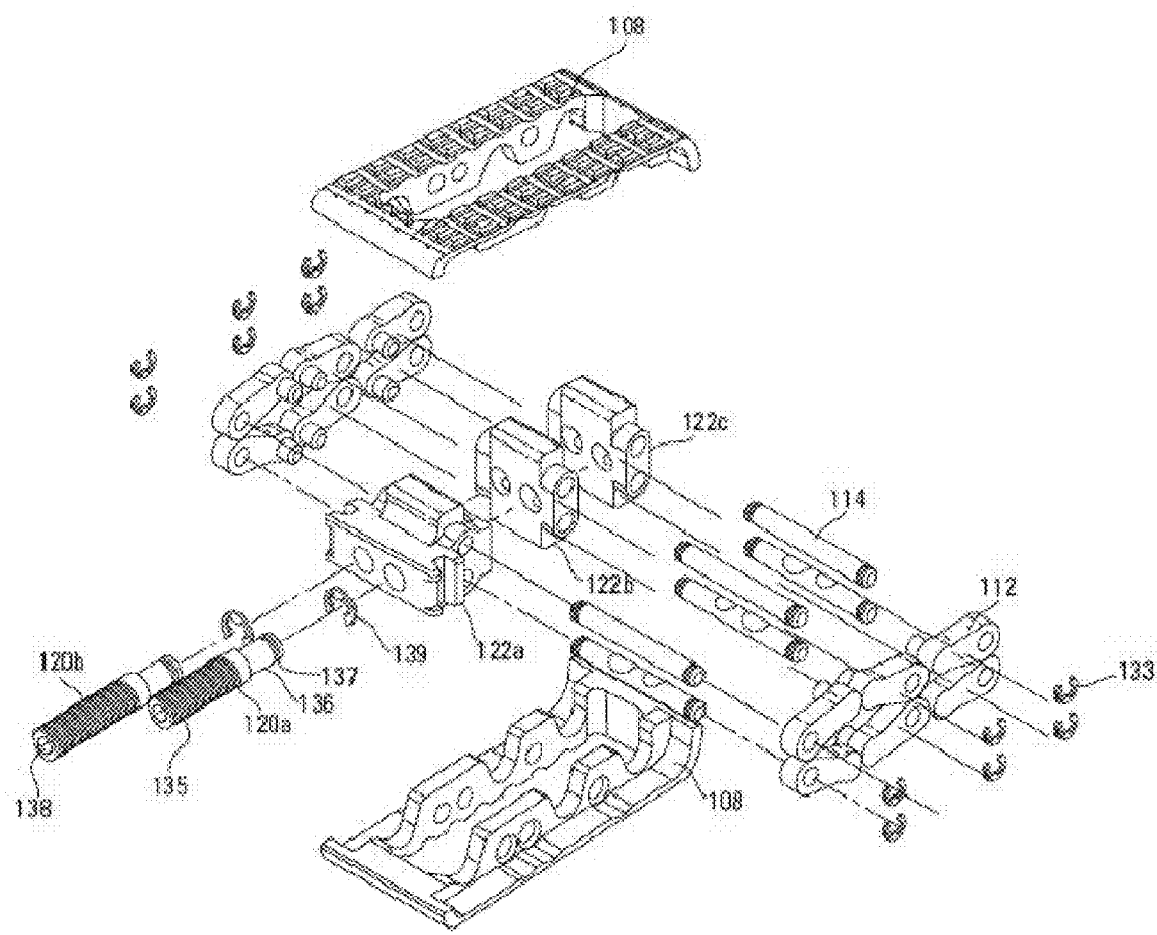
FIG. 16 is an exploded view of an embodiment of an expandable intervertebral cage device according to an aspect of the present invention.

Referring to FIG. 16, in one embodiment, device 100 can include a first actuation member 120a and a second actuation member 120b. In one embodiment, actuation members 120a and 120b can be substantially identical. In one embodiment, actuation member 120 can include a threaded portion 135 of a diameter sized to threadedly couple with longitudinal bore 126 of one or more blocks 122. Actuation member 120 can include a second non-threaded portion 136 having a smaller diameter than threaded portion 135. One end of actuation member 120 can be defined by a slot or socket 138 structured to receive a tool for driving actuation device 120. In one embodiment, socket 138 can be capable of receiving a hex key or Allen wrench, for example, for rotatably driving actuation device 120. In one embodiment, actuation member 120 can include a slot 137 proximate one end of actuation member 120 sized to accept snap ring 139 that can lock actuation members in axial position relative to blocks. Alternatively, snap ring 139 can be located at the proximal end of block 122c, which provides further stability to the screw and reduces the stress on the snap ring.

In one embodiment, first actuation member 120a can extend through first arm assembly 110a into second arm assembly 110a. For example, first actuation member 120a can be threadedly coupled to first arm assembly 110a and rotationally coupled to second arm assembly 110b. Second actuation member 120b can extend through second arm assembly 110a into third arm assembly 110c. For example, second actuation member 120a can be threadedly coupled to second arm assembly 110b and rotationally coupled to third arm assembly 110c.

Figure 17A:
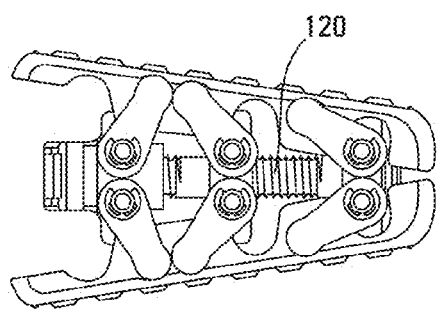
FIGS. 17A-17B are side and perspective views an embodiment of an expandable intervertebral cage device according to an aspect of the present invention in a distracted state, wherein the nose portion is further distracted that the rear portion.
Figure 17B:
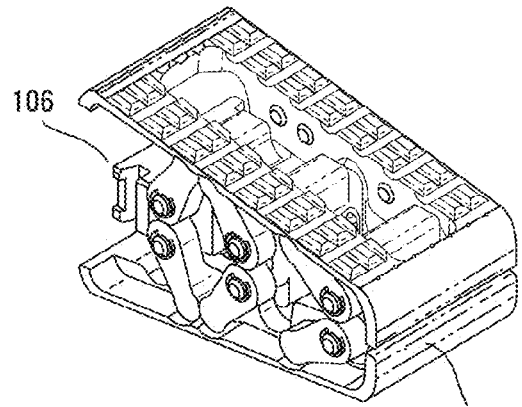
Figure 18A:
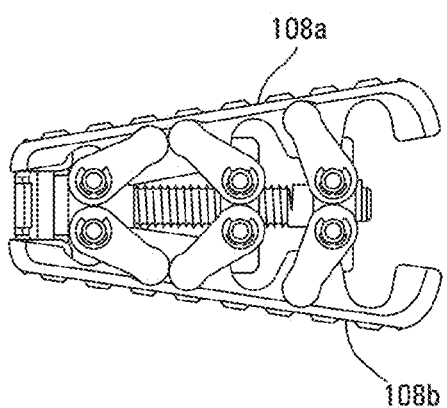
FIGS. 18A-18B are side and perspective views an embodiment of an expandable intervertebral cage device according to an aspect of the present invention in a distracted state, wherein the rear portion is further distracted that the nose portion.
Figure 18B:
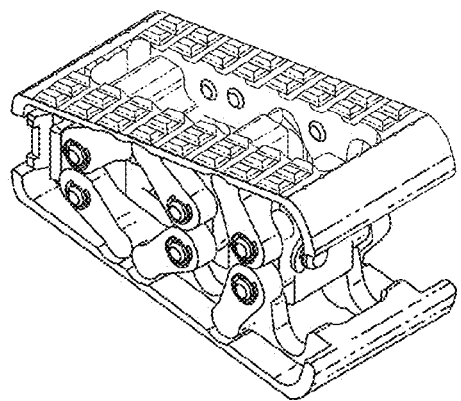
Figure 19A:
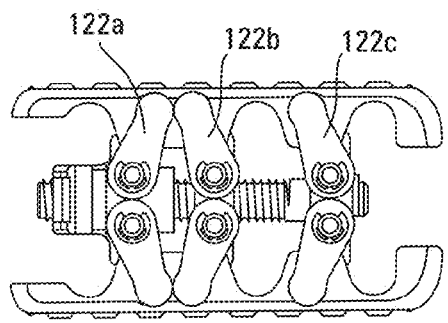
FIGS. 19A-19B are side and perspective views of an embodiment of an expandable intervertebral cage device according to an aspect of the present invention in a distracted state, wherein the rear portion and nose portion are substantially equally distracted.
Figure 19B:
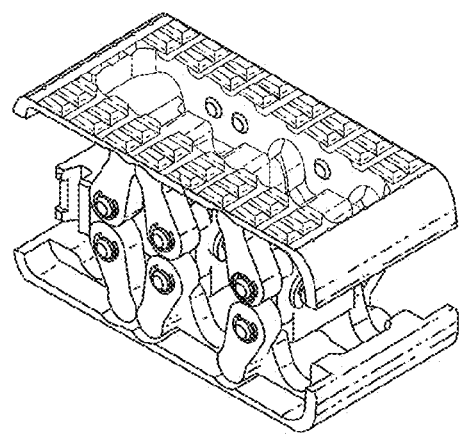

As shown in FIGS. 17A-17B, in one embodiment, actuation of first actuation member 120a in a first direction drives blocks 122a and 122b closer together, which causes expansion of arm assemblies 110a and 110b and distraction of base plates 108. As shown in FIGS. 17A-17B, actuation of second actuation member 120b in a first direction drives blocks 122b and 122c closer together, which causes expansion of arm assemblies 110a and 110b and distraction of base plates 108.

First actuation member 120a and second actuation member 120b are capable of being actuated independently of each other. This independent actuation allows for angular orientation of the base plates 108 to be matched exactly to the unique alignment, or desired planar alignment, of adjacent vertebrae of a patient's spine. Examples of various possible angular orientations of base plates 108 in the distracted state can be seen at FIGS. 17A-17B. Such angulations can be done when the device is expanded within the disc space, enabling the device to go between lordotic and kyphotic angles while in the disc space so that the surgeon can adjust as needed to correct the deformity based on observations made during the procedure.

Conversely, actuation of first actuation member 120a in the opposite direction drives blocks 122a and 122b apart, thereby bringing base plates 108 closer together. Likewise, actuation of second actuation member 120b in the opposite direction drives blocks 122b and 122c apart, thereby bringing base plates 108 closer together. This back-drivability of the device 100 is helpful for sizing the device 100 and removing the device 100 if necessary, such as in the event of post-surgical infection, trauma, or failure to fuse.

Referring again to FIG. 16, non-threaded portion 136 of actuation member 120 and its respective rotational coupling to block 122 enable device 100 to allow for additional distraction due to in-vivo axial tension. For example, the rotational coupling can be constructed with sufficient clearance to allow block 122b to temporarily slide closer to 122a, or block 122c to temporarily slide closer to block 122b. However, having distracted slightly under tensile loading the device would return to the original height as compressive loading is returned. The parallelism would remain unchanged, while lordotic endplates may undergo a small angular displacement that would return to the set lordosis with the reapplication of the normal compressive loading. This extensibility of device 100 could offer great benefits to the fusion process as the endplates, which may be growing into the endplates of the vertebral bodies, would not be pulled away from the endplates by motion of the patient's spine, damaging early bone growth.

In another embodiment, in place of non-threaded portion 136 and snap ring 139, portions of the actuation member 120 can be reverse threaded to allow distraction without changing the position of the threaded members along the respective axes of the threaded members helping to keep the device from adversely interacting with the anatomy of the patient.

In various embodiments, device body 102 is shaped to be ergonomic. Device body 102 can have various shapes, such as, for example, rectangular or kidney-shaped. A kidney-shaped device body 102 maximizes contact between the device and the vertebral bodies because the base plates of vertebrae tend to be slightly concave. One or both ends of the device may also be tapered to facilitate insertion. This minimizes the amount of force needed to initially separate the vertebral bodies. In addition, the device may be convex along both its length and its width, or bi-convex. Device body can also be comprised of various materials. Such materials can include, for example, titanium, steel, PEEK, carbon fiber and cobalt chromium. The device can also be constructed in various sizes depending on the type of vertebra and size of patient with which it is being used, for example, specifically for an anterior lumbar interbody fusion, oblique or a lateral interbody fusion. In some embodiments, the threaded member 120 can be micromachined or split along its length and reconnected using a bellows or flexible torque transmission device, to be able to operate through an angle that may be necessitated by the shape of the device.

In one embodiment, a locking mechanism can be utilized to prevent rotation of the threaded members to ensure the device remains in the distracted state. In one embodiment, the locking mechanism can be activated with the insertion device. In one embodiment, locking may be enhanced by tightening a threaded nut (not shown) against one or more of the blocks 122.

Figure 20:
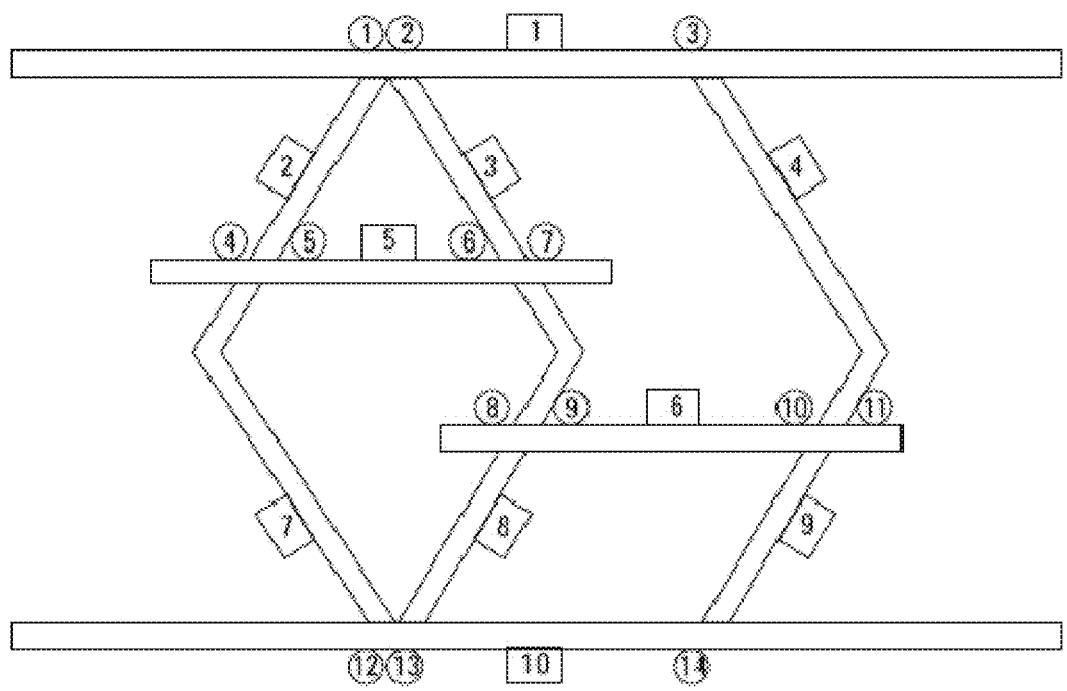
FIG. 20 is a simplified view of an embodiment of an expandable intervertebral cage device according to an aspect of the present invention.

As is demonstrated by a simplified form of device 100 shown in FIG. 20, device 100 can stably support the disc space because it has negative one degree of freedom once locked in the distracted position with actuation members 120 in place. From Gruebler's equation, the number of degrees of freedom=3*(n−1)−2f, where n is the number of links in the linkage and f is the number of one degree of freedom kinematic pairs in the linkage. As is shown in FIG. 20, the device 100 has 10 links and 14 kinematic pairs, so 3*(10−1)−2*14=−1 degrees of freedom. The device is therefore actually over constrained (meaning that there are additional constraints beyond the minimum necessary to make it stable), and stable under loading conditions. This allows device 100 to stably support the disc space upon distraction. In some embodiments, a crush surface or compliant materials may be used in concert with structure to minimize hysteresis that may be present in the device and due to clearance in arm assemblies 112 necessary for overcoming the over-constraint in devices having fewer than zero degrees of freedom due to redundant constraints.

Figure 10A:
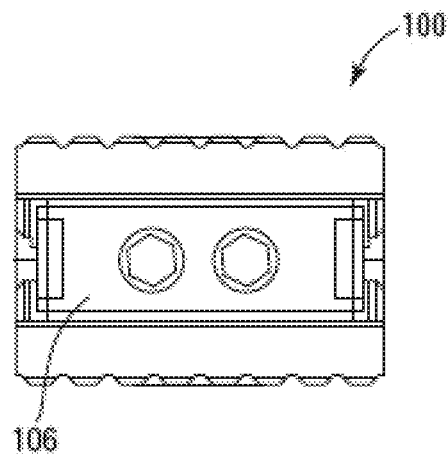
FIG. 10A is a rear view of an embodiment of an expandable intervertebral cage device according to an aspect of the present invention.
Figure 10B:
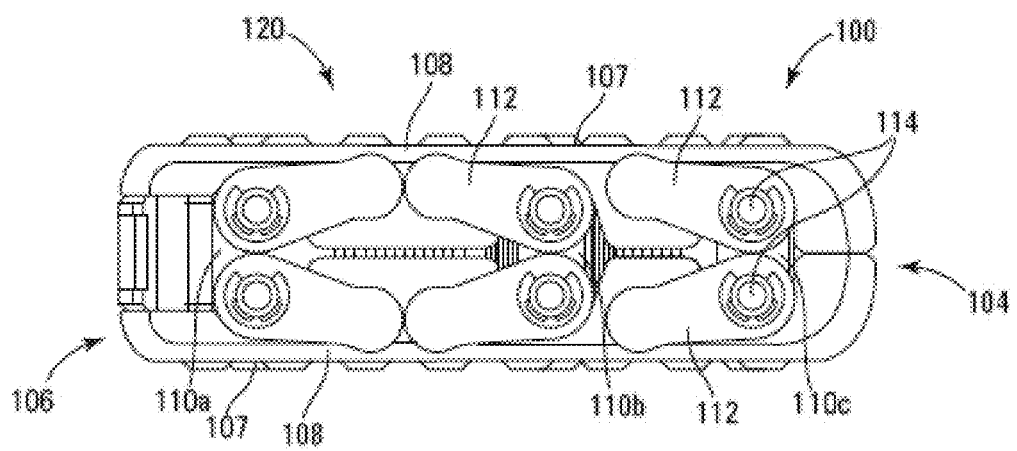
FIG. 10B is a side view of an embodiment of an expandable intervertebral cage device according to an aspect of the present invention.
Figure 10C:
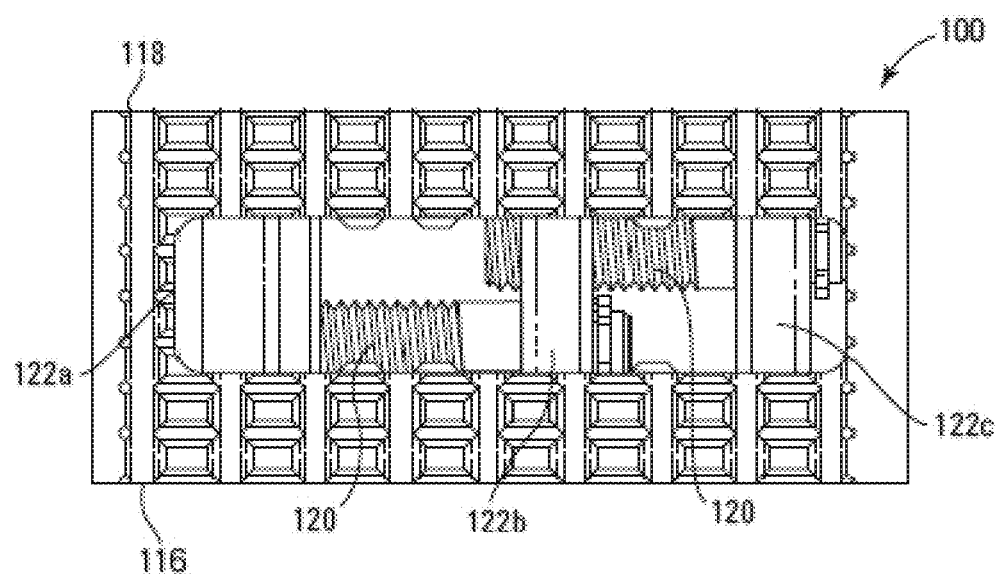
FIG. 10C is a top view of an embodiment of an expandable intervertebral cage device according to an aspect of the present invention.
Figure 11:
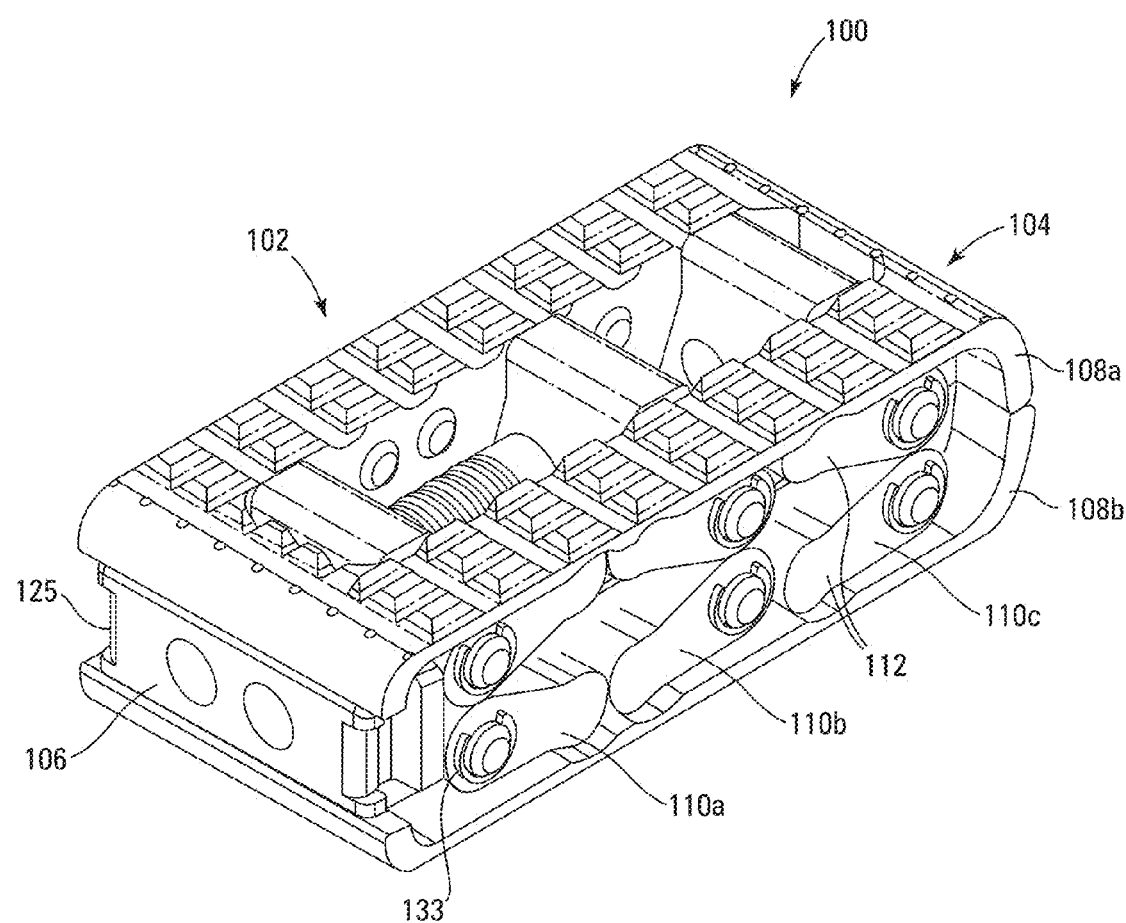
FIG. 11 is a perspective view of an embodiment of an expandable intervertebral cage device according to an aspect of the present invention.

In operation, device 100 can be placed between adjacent vertebrae or vertebral bodies and used to distract the endplates of the adjacent vertebral bodies and subsequently serve as a fusion device. One or more insertion tools (not depicted) can be used to insert and distract device 100. Referring to FIGS. 10A, 10B and 11, the device body 102 can be seen in its initial compressed configuration. In FIGS. 17A-19B, device body 102 is in various expanded configurations. The insertion tool can be connected to actuation members 120 with the proximal block 122a and first used to insert device 100 into a desired location. Device 100 can be inserted with tapered nose portion 104 first. One device 100 can be inserted, or, for additional support, two devices 100 can be inserted. Two devices 100, each sized to be inserted within one-half of the evacuated disc space, can be especially useful for treating larger patients in which the device may encounter higher loads. In another embodiment, three or more small devices can be inserted into the disc space in order to very accurately control the orientation and distance between the discs. Three or more distraction mechanisms may be positioned circumferentially between two circular endplates to result in very accurate control and orientation of the base plates. Such a device would resemble a hexapod.

To distract device 100, an insertion tool can be used to rotate actuation members 120 in a first direction. Actuation of threaded member 120a in a first direction drives blocks 122a and 122b closer together, which causes distraction of base plates 108. Likewise, actuation of threaded member 120b in a first direction drives blocks 122b and 122c closer together, which causes distraction of base plates 108. Actuation of threaded members 120a and 120b in the opposite direction respectively drives blocks 122a and 122b and blocks 122b and 122c apart, thereby bringing base plates 108 closer together.

Once base plates 108 are distracted to a desired degree, insertion tools can be disconnected from threaded members 120 and the device 100 can remain within the body. In one embodiment, a locking mechanism can be utilized to prevent rotation of the threaded members to ensure the device remains in the distracted state.

Once device is inserted and supporting the adjacent vertebral bodies, it can be utilized to promote vertebral fusion. Following distraction, a bone growth stimulant, such as autograft, bone morphogenic protein, or bone enhancing material, can be delivered into an open area defined within the device. In one embodiment, bone growth stimulant is delivered after insertion tools are disconnected. In another embodiment, bone growth stimulant is delivered through an open area between insertion tools. In a further embodiment, bone growth stimulant can be delivered through a hollow chamber within the insertion tools. Device is capable of supporting in-vivo loads during the 6 to 12 weeks that fusion occurs between the vertebral bodies. In one embodiment, openings 124 in base plates 108 promote and allow for bone growth into and through the device 100.

In some embodiments, when the device is implanted and in the process of being expanded, as blocks come closer together the blocks compress the bone graft or bone fusion material that can be inserted inside device to force the material out of the internal chamber of the device an in the adjacent vertebral end plates. This will enhance bone integration into the end plates. Some bone material will remain within the cage, which will integrate and fuse the center of the cage to the top and bottom of the end plates. In certain embodiments, the bone material can be injected into the device through one of the longitudinal holes in the proximal block of the device that does not have an actuation member therethrough. This could be done with the inserter device or separate extended syringe. In some embodiments, the top and bottom base plates of the device can be coated to enhance bone integration.

In an alternative embodiment, a pin can extend vertical through the device to stabilize the proximal end of the device. Such a device could be expanded utilizing only a distal set of arm assemblies and would provide only lordotic angles. Alternatively the pin could stabilize the distal end of the device, which could then be expanded with a single screw and one or more proximally located arm assemblies to provide kyphotic angles.

Although the various devices described herein are described as being brought from a compressed configuration to an expanded configuration by rotation of a threaded member, the devices can be distracted by any other type of actuation member. In some embodiments, mechanisms other than threaded members can be used to distract the device. Such mechanisms include, for example, a pop-rivet mechanism, a sardine key and ribbon, a tourniquet and wire, a saw blade/ratchet, a zip-tie-like mechanism, piezo-electric inch worm motors and shape changing materials such as a shape member alloy or a conducting polymer actuator. These alternative locking mechanisms could be designed to make the device behave as if it were locked with a threaded member, preventing the device from being compressed as well as extended, or these mechanisms could afford the device the capability to ratchet upwards post implantation if such action would benefit the patient or provide additional therapy.

Various embodiments of implantation procedures for the disclosed embodiments of expandable intervertebral cage devices may be as follows:

Lumbar: A lumbar implant can be 8 mm in height, expandable to 14 mm in height, with a length of 25-30 mm and a width of 10-12 mm. The implant can be inserted through a minimally invasive tubular port that goes through the muscle of the lumbar spine and into the lumbar disc space. Prior to inserting the implant, the lumbar disc should be completely removed. Other embodiments for the lumbar spine include larger sizes for anterior, posterior, transforaminal, oblique lateral, and lateral interbody fusions.

Cervical: A cervical implant can be 6 mm in height, expandable to 10 mm in height, with a length of 10 mm and a width of 6 mm. The implant can be inserted after anterior cervical surgical exposure. The cervical disc should be completely removed prior to insertion of the implant.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. An expandable intervertebral cage device adapted to be implanted into an intervertebral disc space in a patient's body, comprising:
    a first base plate having a first outer bearing surface configured to interface with a first vertebra of the intervertebral disc space;
    a second base plate having a second outer bearing surface configured to interface with a second vertebra of the intervertebral disc space;
    a proximal block mechanically coupled to the first base plate and the second base plate, wherein the proximal block comprises internal threading;
    a distal block comprising an internal passage;
    only two arm assemblies, wherein a first one of the two arm assemblies is arranged on a first side of the device and a second one of the two arm assemblies is arranged on a second side of the device, wherein each of the only two arm assemblies comprises:
        only a first arm and a second arm, including
            the first arm pivotally coupled to the first base plate and the distal block; and
            the second arm pivotally coupled to the second base plate and the distal block; and
    a screw arranged partially within the internal threading of the proximal block and passing through the internal passage of the distal block, such that rotation of the screw relative to the proximal block causes a change in distance between the proximal block and the distal block, and a corresponding change in the spacing and lordosis of the device due to an expansion or contraction of the arm assemblies, and wherein the screw is threadedly coupled to the internal threading of the proximal block, and the distal block includes a non-threaded rotational coupling to which the screw is non-threadedly rotationally coupled.

2. The device of claim 1, further comprising a rod passing through the proximal block and the first base plate to attach the proximal block to the first base plate while permitting relative rotation therebetween.

3. The device of claim 2, further comprising a rod passing through the proximal block and the second base plate to attach the proximal block to the second base plate while permitting relative rotation therebetween.

4. The device of claim 1, wherein the first base plate and the second base plate each have an opening defined therein configured to allow bone growth into an open space defined by the device.

5. The device of claim 1, wherein the screw includes a first portion having a first diameter and a second portion having a second diameter.

6. The device of claim 5, wherein the first portion of the screw has a diameter adapted to pass through the internal threading of the proximal block and the second portion of the screw has an opening adapted to pass through the internal passage of the distal block.

7. The device of claim 1, wherein rotation of the screw relative to the proximal block further causes the arm assemblies to expand to angle the first base plate and the second base plate relative to each other.

8. The device of claim 7, wherein a distance between a proximal end of the first base plate and a proximal end of the second base plate remains constant as the arm assemblies are expanded.

9. An expandable intervertebral cage device adapted to be implanted into an intervertebral disc space in a patient's body, comprising:
    a first base plate having a first outer bearing surface configured to interface with a first vertebra of the intervertebral disc space;
    a second base plate having a second outer bearing surface configured to interface with a second vertebra of the intervertebral disc space;
    a proximal block mechanically coupled to the first base plate and the second base plate, wherein the proximal block comprises internal threading;
    a distal block comprising an internal passage;
    only a single arm assembly extending between the first base plate and second base plate on each of a first side of the device and second side of the device, each arm assembly including only a pair of arms with a first arm of the pair of arms pivotally coupled to the first base plate and a second arm of the pair of arms pivotally coupled to the second base plate and the first arm and second arm are each coupled to the distal block; and
    a screw device extending longitudinally between the first base plate and the second base plate, wherein rotation of the screw device in a first direction causes the arm assemblies to expand and rotation of the screw device in a second direction causes the arm assemblies to contract by changing a distance between the proximal block and the distal block, and wherein expansion of the arm assemblies causes the first base plate and the second base plate to be angled relative to one another, and
    wherein the screw device is threadedly coupled to the internal threading of the proximal block, and the distal block includes a non-threaded rotational coupling to which the screw device is non-threadedly rotationally coupled.

10. The device of claim 9, wherein a distance between a proximal end of the first base plate and a proximal end of the second base plate remains constant as the arm assemblies are expanded.

11. The device of claim 9, wherein at a maximum expansion of the arm assemblies each base plate defines an angle of approximately 23 degrees.

12. A method comprising:
providing an expandable intervertebral cage device, comprising:
  a first base plate having a first outer bearing surface;
  a second base plate having a second outer bearing surface;
  a proximal block mechanically coupled to the first base plate and the second base plate, wherein the proximal block comprises internal threading;
  a distal block comprising an internal passage;
  only two arm assemblies, wherein a first one of the two arm assemblies is arranged on a first side of the device and a second one of the two arm assemblies is arranged on a second side of the device, wherein each of the only two arm assemblies comprises:
    a first arm pivotally coupled to the first base plate and the distal block; and
    a second arm is pivotally coupled to the second base plate and the distal block; and
  a screw arranged partially within the internal threading of the proximal block and passing through the internal passage of the distal block, such that rotation of the screw relative to the proximal block causes a change in distance between the proximal block and the distal block, and a corresponding change in the spacing and lordosis of the device due to an expansion or contraction of the arm assemblies, and
wherein the screw is threadedly coupled to the internal threading of the proximal block, and the distal block includes a non-threaded rotational coupling to which the screw is non-threadedly rotationally coupled; and
inserting the expandable intervertebral cage device into an intervertebral disc space of a patient defined between adjacent vertebrae such that the first bearing surface interfaces with an end plate of a superior vertebra of the intervertebral disc space and the second bearing surface interfaces with an end plate of an inferior vertebra of the intervertebral disc space;
expanding the device within the intervertebral disc space into an expanded configuration by rotating the screw relative to the proximal block; and
leaving the device within the intervertebral disc space following insertion and expansion.

13. The method of claim 12, wherein expanding the device includes angling the first base plate and second base plate relative to each other.

14. The method of claim 13, wherein expanding the device includes maintaining a constant distance between a proximal end of the first base plate and a proximal end of the second base plate.

15. The method of claim 13, wherein expanding the device includes angling each base plate to define an angle of approximately 23 degrees.

16. The method of claim 12, further comprising inserting a bone growth material into an open area within the device.

* * * * *